(12) United States Patent
English et al.

(10) Patent No.: US 10,344,320 B2
(45) Date of Patent: Jul. 9, 2019

(54) CAPACITIVE LIQUID CRYSTAL BIOSENSORS

(71) Applicant: The Johns Hopkins University, Baltimore, MD (US)

(72) Inventors: Emily P. English, Ellicott City, MD (US); David B. Taubenheim, Silver Spring, MD (US); Christopher E. Bradburne, Arlington, VA (US); Matthew P. Yeager, Washington, DC (US); Jason E. Tiffany, Columbia, MD (US); Leslie H. Hamilton, Takoma Park, MD (US)

(73) Assignee: The Johns Hopkins University, Baltimore, MD (US)

( * ) Notice: Subject to any disclaimer, the term of this patent is extended or adjusted under 35 U.S.C. 154(b) by 441 days.

(21) Appl. No.: 15/146,914

(22) Filed: May 5, 2016

(65) Prior Publication Data
US 2016/0327506 A1    Nov. 10, 2016

Related U.S. Application Data

(60) Provisional application No. 62/157,646, filed on May 6, 2015.

(51) Int. Cl.
*C12Q 1/6825* (2018.01)
(52) U.S. Cl.
CPC .................................. *C12Q 1/6825* (2013.01)
(58) Field of Classification Search
CPC .................................................. C12Q 1/6825
See application file for complete search history.

(56) References Cited

U.S. PATENT DOCUMENTS

| | | |
|---|---|---|
| 6,485,905 B2 | 11/2002 | Hefti |
| 7,531,366 B2 | 5/2009 | Abbott et al. |
| 2007/0042505 A1* | 2/2007 | Israel ..................... B82Y 30/00 436/518 |

OTHER PUBLICATIONS

Harmon, P., University of Florida, Department of Plant Pathology, "PCR, Detection Times Compared to ELISA," Epub (2005), available online at http://www.plantmanagementnetwork.org/infocenter/topic/soybeanrust/symposium/presentations/Harmon (last accessed Feb. 2, 2016), pp. 1-15.

(Continued)

*Primary Examiner* — Robert J Eom
(74) *Attorney, Agent, or Firm* — Noah J. Hayward

(57) ABSTRACT

A capacitive liquid crystal (LC) biosensor for sensing a target biological agent includes a support board; a flow channel on the support board, the flow channel having an inlet port at a first end and an exit port at a second end; at least two electrodes, the at least two electrodes including a first electrode on a flow channel first surface and a second electrode on a flow channel second surface opposite the flow channel first surface; an electricity source connected to the first electrode and the second electrode; and an LC sensor array positioned within the flow channel. An LC sensor array includes a sensor support surface; wells positioned on the sensor support surface; an organic LC phase within each of the plurality of wells; and an aqueous phase having an analyte positioned above the organic LC phase within the wells.

19 Claims, 16 Drawing Sheets

(56) References Cited

OTHER PUBLICATIONS

Unknown, "Liquid crystal biosensor technology promises real-time pathogen detection," Homeland Security News Wire, Mar. 2, 2006, available online at http://www.homelandsecuritynewswire.com/liquid-crystal-biosensor-technology-promises-real-time-pathogen-detection (last accessed Feb. 2, 2016), p. 1.

Namkung, Jun, "Novel Capacitive Microstructures for Chemical and Biological Sensors Using Liquid Crystals," University of Alabama in Huntsville Dissertation, 3438425 (2010), pp. iv-138.

Crawford, Gregory, "Liquid Crystal Biosensors A New Approach to Medical Diagnostic Devices," Chapter 4 (excerpt only) from Liquid Crystals: Frontiers in Biomedical Applications, World Scientific Publishing Co. (2007), available online at http://www.globalspec.com/reference/49719/203279/chapter-4-liquid-crystal-biosensors-a-new-approach-to-medical-diagnostic-devices (last accessed Feb. 2, 2016), pp. 1-3.

Berggren, C. et al., "Review: Capacitive Biosensors," Department of Analytical Chemistry, Chemical Center, University of Lund, Sweden (Jul. 7, 2000), pp. 173-180.

* cited by examiner

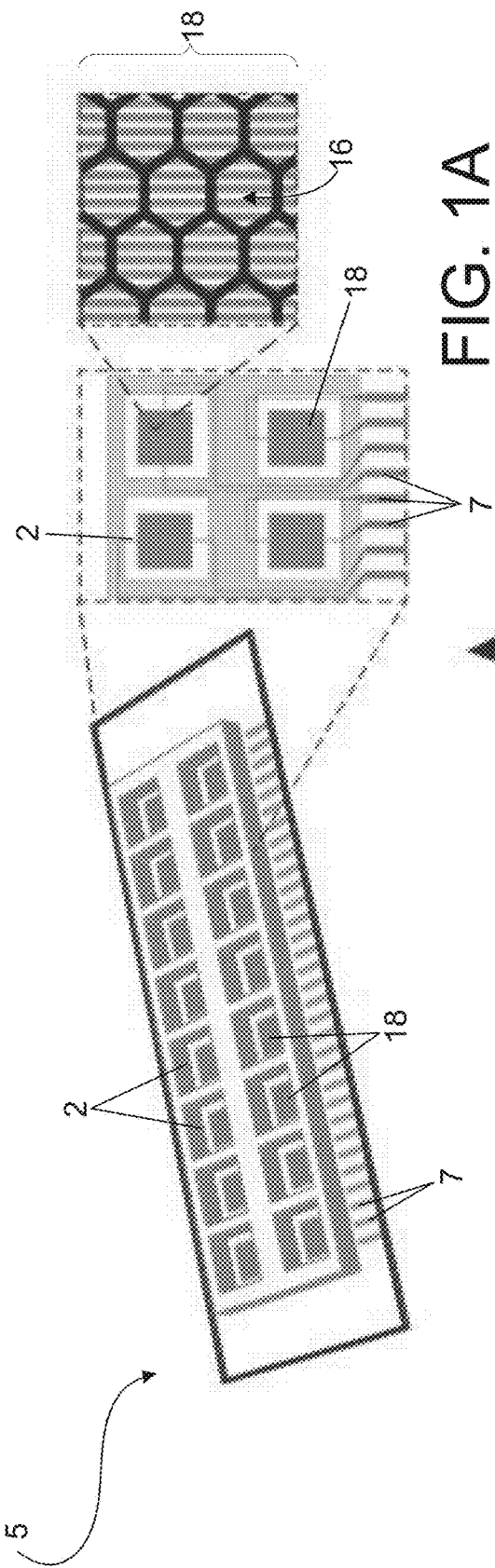
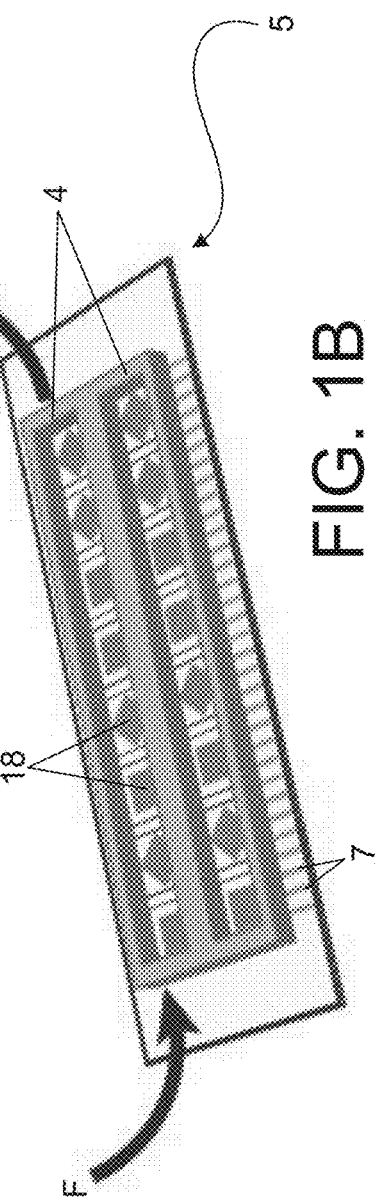
FIG. 1A
FIG. 1B

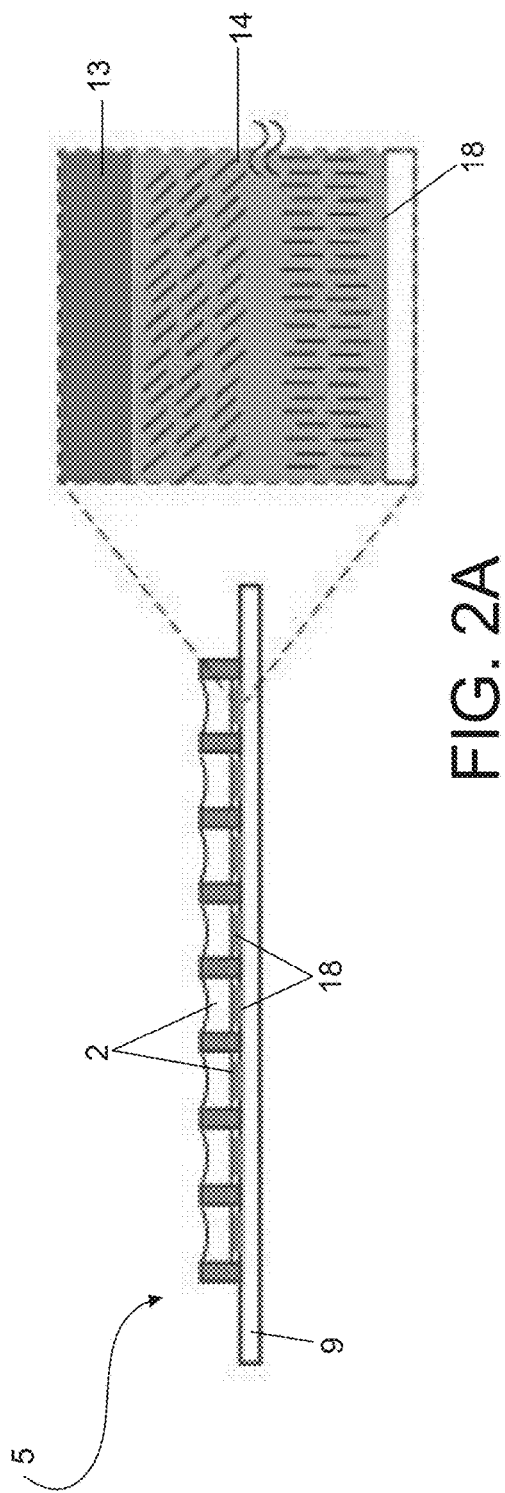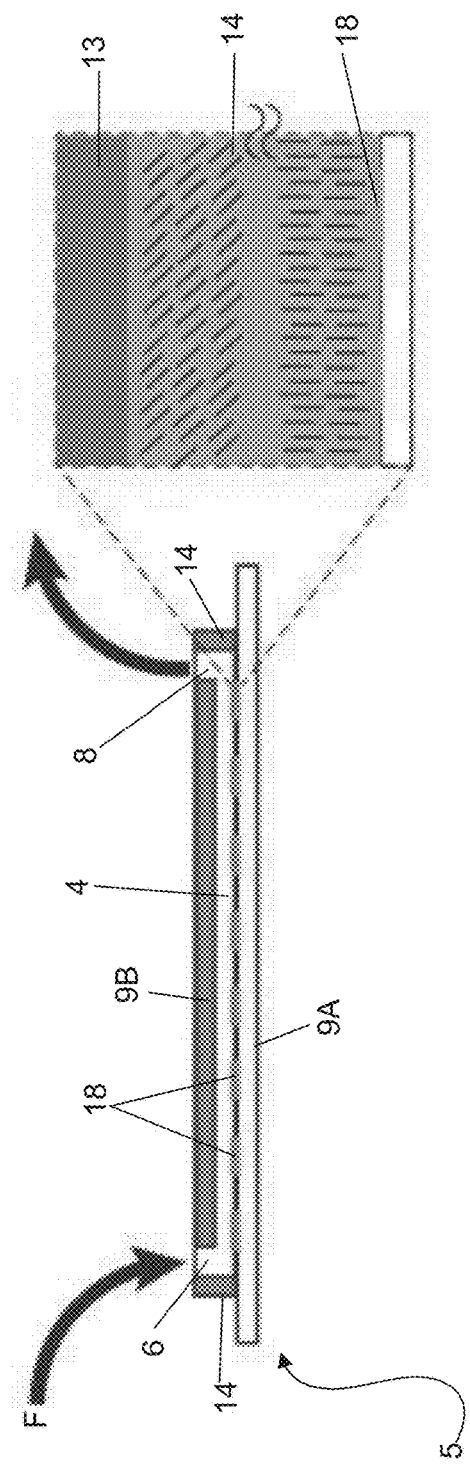
FIG. 2A
FIG. 2B

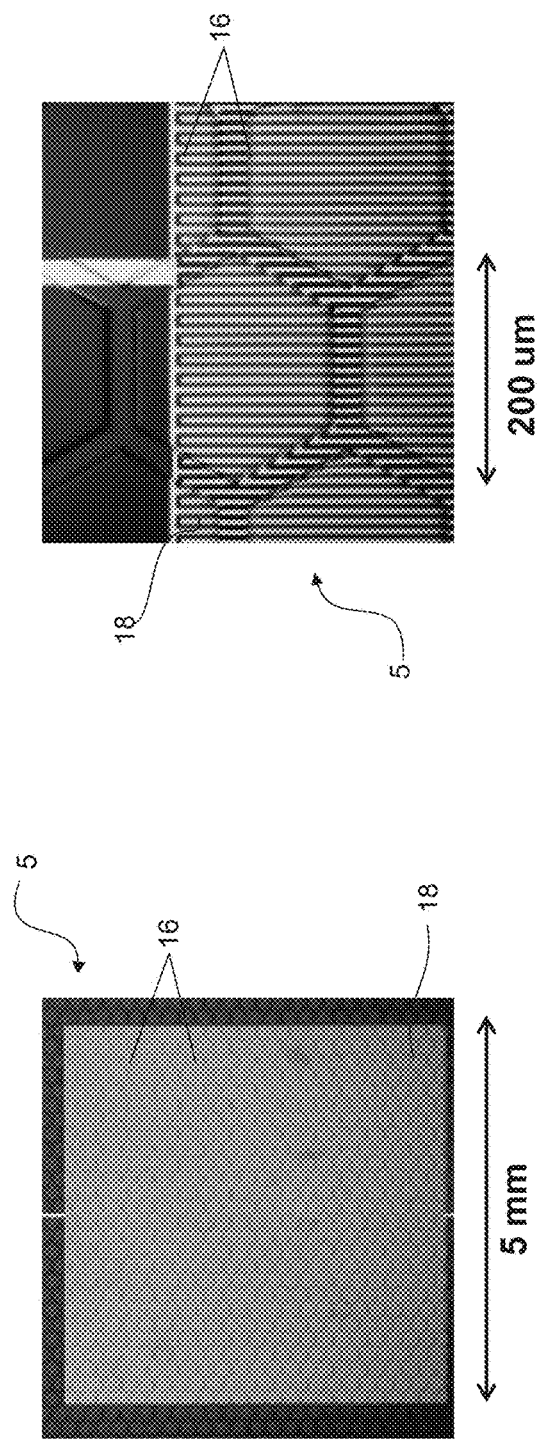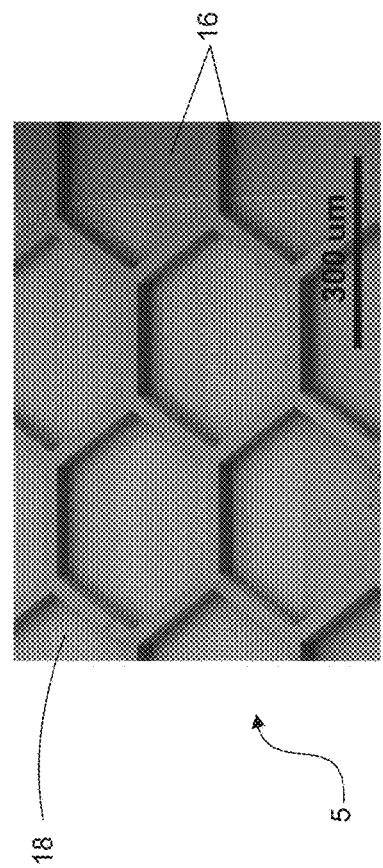
FIG. 3A
FIG. 3B
FIG. 3C

CAPACITIVE LIQUID CRYSTAL BIOSENSORS

CROSS-REFERENCE TO RELATED APPLICATIONS

This application claims the benefit of U.S. Provisional Application No. 62/157,646 filed on May 6, 2015, the entire contents of which are hereby incorporated herein by reference.

TECHNICAL FIELD

Example embodiments relate generally to capacitive liquid crystal (LC) biosensors.

BACKGROUND

The use of sensors in the healthcare sector is mainly driven by the increasing need for sophistication in medical electronics to "sense" and "monitor" temperatures, pressures, chemical, and biological levels of patients and drugs for applications in diagnostics, therapeutics, monitoring, drug discovery and delivery; in hospitals and other medical facilities, including home-treatments. Sensors play an important role in enhancing safety and improving the quality of life in the healthcare arena. Sensors are increasingly being used in medical applications due to accuracy, intelligence, capability, reliability, small size, and low power consumption of sensors. Sensors increase the intelligence of the life supporting implants. They can also be used in various types of monitoring appliances to provide better quality of life for the patients. Sensors enable early detection of ailments, thereby allowing a timely prevention or cure. Moreover, sensors may be used for detection of environmental hazards and chemical agents. Most existing liquid crystal detection measure changes in optical features, such as refractive indices. However, the examination of these changes is time consuming, expensive, and requires specialized equipment.

Therefore there at least remains a need in the art for a lightweight, portable, cost-effective liquid crystal biosensor for identifying a target biological agent(s) and methods of operating thereof.

BRIEF SUMMARY

One or more example embodiments may address one or more of the aforementioned problems. Certain example embodiments provide a capacitive liquid crystal (LC) biosensor for sensing a target biological agent. In accordance with certain embodiments, the capacitive LC biosensor may comprise a support board; a flow channel positioned on the support board, the flow channel having an inlet port positioned at a first end and an exit port positioned at a second end; at least two electrodes, the at least two electrodes comprising a first electrode disposed on a flow channel first surface and a second electrode disposed on a flow channel second surface opposite the flow channel first surface; an electricity source connected to the first electrode and the second electrode; and an LC sensor array positioned within the flow channel. The LC sensor array may comprise a sensor support surface; a plurality of wells positioned on the sensor support surface; an organic LC phase positioned within each of the plurality of wells; and an aqueous phase comprising an analyte positioned above the organic LC phase within the plurality of wells.

In another aspect, a capacitive LC biosensor device is provided. The device may comprise an exterior portion comprising a display and an interior portion comprising a capacitive LC biosensor, a sample input portion upstream of the capacitive LC biosensor, and a wicking cap downstream of both the sample input portion and the capacitive LC biosensor. The capacitive LC biosensor may comprise a support board; a flow channel positioned on the support board, the flow channel having an inlet port positioned at a first end and an exit port positioned at a second end; at least two electrodes, the at least two electrodes comprising a first electrode disposed on a flow channel first surface and a second electrode disposed on a flow channel second surface opposite the flow channel first surface; an electricity source connected to the first electrode and the second electrode; and an LC sensor array positioned within the flow channel. The LC sensor array may comprise a sensor support surface; a plurality of wells positioned on the sensor support surface; an organic LC phase positioned within each of the plurality of wells; and an aqueous phase comprising an analyte positioned above the organic LC phase within the plurality of wells.

In yet another aspect, a method for sensing a target biological agent is provided. The method may comprise providing a capacitive LC biosensor, adding a sample to the capacitive LC biosensor, and identifying whether a state change occurred in association with adding the sample to the capacitive LC biosensor in order to determine whether the target biological agent is present in the sample.

BRIEF DESCRIPTION OF THE DRAWING(S)

Having thus described example embodiments in general terms, reference will now be made to the accompanying drawings, which are not necessarily drawn to scale, and wherein:

FIGS. 1A and 1B illustrate perspective views of liquid crystal (LC) sensor arrays according to example embodiments;

FIGS. 2A and 2B illustrate side views of LC sensor arrays according to example embodiments;

FIGS. 3A-3C illustrate varying magnifications of top views of an LC sensor array according to an example embodiment;

DETAILED DESCRIPTION

Figure 4A:
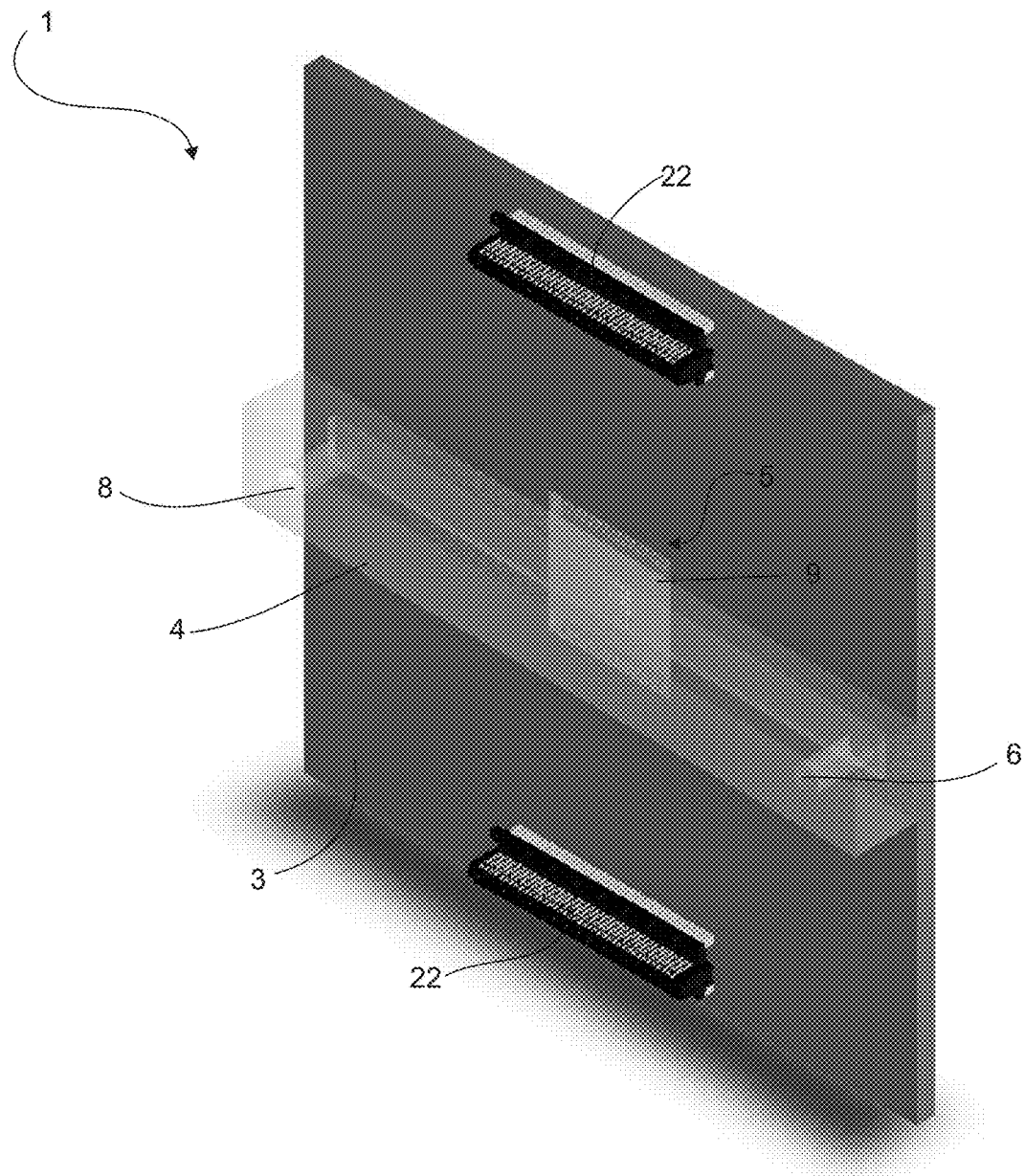
FIG. 4A illustrates a perspective view of a capacitive LC biosensor that includes onboard electronics according to an example embodiment.

Some example embodiments now will be described more fully hereinafter with reference to the accompanying drawings, in which some, but not all embodiments are shown. Indeed, the examples described and pictured herein should not be construed as being limiting as to the scope, applicability, or configuration of the present disclosure. Rather, these example embodiments are provided so that this disclosure will satisfy applicable legal requirements. Like reference numeral refer to like elements throughout. As used in the specification, and in the appended claims, the singular forms "a", "an", "the", include plural referents unless the context clearly dictates otherwise.

Certain example embodiments provide a capacitive liquid crystal (LC) biosensor for sensing a target biological agent. For instance, this capacitive LC biosensor may provide, for example, lightweight, portable, cost-effective platform for identifying a target biological agent(s) based on, for example, nucleic acid, proteins, and small molecules. In addition, the capacitive LC biosensor may be applied in small, portable, and disposable diagnostic devices. Moreover, the capacitive LC biosensor may be applied to develop autonomous sensors for environmental monitoring applications. As such, by way of example only, the capacitive LC biosensor may be sensitive, selective, rapid, label-free, portable, remotely operated without a lab infrastructure, inexpensive (e.g., for single use devices), analyte agnostic, and/or multiplexed.

Although particular viruses, bacteria, toxins, and/or the like are frequently referenced throughout this disclosure, these particular biological agents serve only as exemplary embodiments, and, as such, this disclosure should not be limited to such biological agents, as other exemplary embodiments could be applicable to a wide variety of biological agents.

I. Definitions

As used herein, the term "liquid crystal" may comprise matter in a state that has properties between those of conventional liquid and those of solid crystal. For instance, a liquid crystal may flow like a liquid, but its molecules may be oriented in a crystal-like manner. There are many different types of liquid-crystal phases, which can be distinguished by their different optical properties (such as birefringence). When viewed under a microscope using a polarized light source, different liquid crystal phases will appear to have distinct textures. The contrasting areas in the textures correspond to domains where the liquid-crystal molecules are oriented in different directions. Within a domain, however, the molecules are well ordered around a single director. Ordering will depend upon the LC molecule and environmental influences. Scientists and engineers are able to use liquid crystals in a variety of applications because external perturbation can cause significant changes in the macroscopic properties of the liquid crystal system. Both electric and magnetic fields can be used to induce these changes. The magnitude of the fields, as well as the speed at which the molecules align are important characteristics. As in the case of certain exemplary embodiments, the matching probe and target cause the perturbation which in turn causes the change in the dielectric value of the liquid crystal.

The term "biosensor", as used herein, may comprise an analytical device, used for the detection of an analyte that combines a biological component with a physicochemical detector.

The term "small molecule", as used herein, may comprise a low molecular weight (<900 Daltons) organic compound that may help regulate a biological process, with a size on the order of $10^{-9}$ m. Most drugs are small molecules. The upper molecular weight limit for a small molecule is approximately 900 Daltons, which allows for the possibility to rapidly diffuse across cell membranes so that they can reach intracellular sites of action. In addition, this molecular weight cutoff is a necessary but insufficient condition for oral bioavailability. Finally, a lower molecular weight cutoff of 500 Daltons (as part of the "rule of five") has been recommended for small molecule drug development candidates based on the observation that clinical attrition rates are significantly reduced if the molecular weight is kept below this 500 Dalton limit. Pharmacology usually restricts the term to a molecule that binds to a specific biological target—such as a specific protein or nucleic acid—and acts as an effector, altering the activity or function of the target. Small molecules can have a variety of biological functions, serving as cell signaling molecules, as drugs in medicine, as pesticides in farming, and in many other roles. These compounds can be natural (such as secondary metabolites) or artificial (such as antiviral drugs); they may have a beneficial effect against a disease (such as drugs) or may be detrimental (such as teratogens and carcinogens). Small molecules may also be used as research tools to probe biological function as well as leads in the development of new therapeutic agents. Some can inhibit a specific function of a multifunctional protein or disrupt protein—protein interactions. In addition, the term "small molecule receptor", as used herein, may generally refer to anything that binds with a small molecule as defined above.

The terms "extracting", "extracted", and "extract", as used herein may generally refer to any compatible means of extracting nucleic acids as understood by one of ordinary skill in the art. Certain exemplary embodiments comprise RNA extraction or DNA extraction depending on the application of a given embodiment disclosed herein. RNA extraction, for example, may generally refer to the purification of RNA from biological samples. This procedure is complicated by the ubiquitous presence of ribonuclease enzymes in cells and tissues, which can rapidly degrade RNA. Several methods are used in molecular biology to isolate RNA from samples, the most common of these is Guanidinium thiocyanate-phenol-chloroform extraction.

The terms "lysing", "lysed", and "lyse", as used herein, may generally refer to the breaking down of the membrane of a cell, often by viral, enzymatic, or osmotic mechanisms that compromise its integrity. Cell lysis may be used to break open cells and purify or further study their contents and may be effected by enzymes or detergents or other chaotropic agents.

The terms "multiplex", "multiplexing", and "multiplex assay", as used herein, may generally refer to a type of assay that simultaneously measures multiple analytes (dozens or more) in a single run/cycle of the assay. It is distinguished from procedures that measure one analyte at a time. Multiplex assays are often used in high-throughput screening settings, where many specimens can be analyzed using a multiplex (or other) assay.

The term "amplicon", as used herein, may comprise may comprise a piece of DNA or RNA that is the source and/or product of natural or artificial amplification or replication events. Amplicons in general are direct repeat (head-to-tail) or inverted repeat (head-to-head or tail-to-tail) genetic sequences, and can be either linear or circular in structure. The terms "amplifying", "amplified", "amplify", and "amplification", as used herein, may generally refer to the production of one or more copies of a genetic fragment or target sequence, specifically the amplicon. As the product of an amplification reaction, amplicon is used interchangeably with common laboratory terms, such as PCR product.

The terms "hybridizing", "hybridize", "hybridized", and "hybridization", as used herein, may generally refer to a phenomenon in which single-stranded deoxyribonucleic acid (DNA) or ribonucleic acid (RNA) molecules anneal to complementary DNA or RNA. Though a double-stranded DNA sequence is generally stable under physiological conditions, changing these conditions in the laboratory (generally by raising the surrounding temperature) will cause the molecules to separate into single strands. These strands are complementary to each other but may also be complementary to other sequences present in their surroundings. Lowering the surrounding temperature allows the single-stranded molecules to anneal or "hybridize" to each other. DNA replication and transcription of DNA into RNA both rely upon nucleotide hybridization.

The term "lateral flow assay", as used herein, may comprise simple devices intended to detect the presence (or absence) of a target analyte in sample (matrix) without the need for specialized and costly equipment. The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these stripes, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the absorbent pad, which simply acts as a waste container.

II. Capacitive Liquid Crystal (LC) Biosensor

In some example embodiments, a capacitive liquid crystal (LC) biosensor for sensing a target biological agent is provided. For instance, this capacitive LC biosensor provides a lightweight, portable, cost-effective platform for identifying a target biological agent(s) based on, for example, nucleic acid, proteins, and small molecules. In general, capacitive LC biosensors may include a support board; at least one of a flow channel or a plurality of acrylic wells positioned on the support board, the flow channel having an inlet port positioned at a first end and an exit port positioned at a second end; at least two electrodes, the at least two electrodes comprising a first electrode disposed on a flow channel first surface and a second electrode disposed on a flow channel second surface opposite the flow channel first surface; an electricity source connected to the first electrode and the second electrode; and an LC sensor array positioned within the flow channel. The LC sensor array, for example, may comprise a sensor support surface; a plurality of hexagonal wells positioned on the sensor support surface; an organic LC phase positioned within each of the plurality of wells; and an aqueous phase comprising an analyte positioned above the organic LC phase within the plurality of wells. According to certain exemplary embodiments, for instance, the plurality of hexagonal wells may comprise an epoxy-based negative photoresist (i.e. SU-8) formulated via photolithography.

For example, FIGS. 1A and 1B illustrate perspective views of liquid crystal (LC) sensor arrays according to example embodiments. For instance, FIG. 1A illustrates one embodiment of an LC sensor array 5 having a plurality of individual acrylic wells 2 (e.g., 16 wells), while FIG. 1B illustrates another embodiment of an LC sensor array 5 having a plurality of separate interdigitated electrode pads 18 (e.g., 16 electrodes) positioned within separate flow channels 4. In both FIGS. 1A and 1B, the plurality of electrodes 18 have a plurality of photoresist hexagonal wells 16 positioned thereon. The plurality of photoresist hexagonal wells 16 are configured to confine the liquid crystals for improved visualization of the state change of the liquid crystals during sensing of a target biological agent. The liquid crystals may be any suitable liquid crystal for the applications disclosed herein as understood by one of ordinary skill in the art including, but not limited to, 4-cyano-4'-pentylbiphenyl (5CB), 4-cyano-4-hexylbiphenyl (6CB), 4-(trans-4-n-hexylcyclohexyl) isothiocyanatobenzoate (6-CHBT), E7 liquid crystal eutectic mixture, MLC-15600-100 eutectic mixture from Merck®, MLC-6828 from Merck® and/or the like. In the embodiment illustrated by FIG. 1A, the plurality of acrylic wells 2 are configured to confine a buffer/analyte solution, while in the embodiment illustrated by FIG. 1B, the flow channels 4 are configured to permit the flow of a buffer/analyte solution over the electrodes 18. In addition, the LC sensor array 5 includes a plurality of electrical leads 7 connected to the plurality of electrodes 18 that allow capacitive readout and connection to an electricity source (e.g., batteries, plugged into an electrical socket, etc.).

In accordance with certain exemplary embodiments, for instance, the plurality of electrodes 18 may include at least a first electrode and a second electrode. For example, the first and second electrodes may comprise gold electrodes. In some embodiments, for example, at least one of the first and second electrodes may comprise a gold interdigitated electrode. In embodiments having a flow channel 4, the LC sensor array 5 may include a first electrode disposed on a first surface (i.e. glass microscopic slide 9A) of the flow channel 4 and a second electrode disposed on a second surface (i.e. glass microscopic slide 9B) of the flow channel 4. The electrodes may be disposed parallel to each other or perpendicular to each other within the flow channel 4. In some embodiments, the first electrode may be an interdigitated electrode, while the second electrode is not. However, in other embodiments, for instance, neither electrode may be interdigitated. In such embodiments, both electrodes may be parallel gold electrodes. In some embodiments, one of the electrodes may have direct alkylthiol functionalization.

In accordance with certain exemplary embodiments, for instance, the capacitive LC biosensor may comprise a length from about 1 cm to about 15 cm. In other embodiments, for example, the capacitive LC biosensor may comprise a length from about 5 cm to about 10 cm. In further embodiments, for instance, the capacitive LC biosensor may comprise a length of about 7.5 cm. As such, in certain embodiments, the capacitive LC biosensor may comprise a length from at least about any of the following: 1, 2, 3, 4, 5, 6, 7, and 7.5 cm and/or at most about 15, 14, 13, 12, 11, 10, 9, 8, and 7.5 cm (e.g., about 7-13 cm, about 6-9 cm, etc.). In some embodiments, for example, the capacitive LC biosensor may comprise a width from about 1 cm to about 5 cm. In other embodiments, for instance, the capacitive LC biosensor may comprise a width from about 2 cm to about 3 cm. In further embodiments, for example, the capacitive LC biosensor may comprise a width of about 2.5 cm. As such, in certain embodiments, the capacitive LC biosensor may comprise a width from at least about any of the following: 1, 1.5, 2, and 2.5 cm and/or at most about 5, 4.5, 4, 3.5, 3, and 2.5 cm (e.g., about 1.5-3.5 cm, about 2-3 cm, etc.).

In certain embodiments, for instance, the flow channel comprises a length from about 1 cm to about 10 cm. In other embodiments, for example, the flow channel comprises a length from about 3 cm to about 7 cm. In further embodiments, for instance, the flow channel comprises a length of about 5 cm. As such, in certain embodiments, the flow channel comprises a length from at least about any of the following: 1, 2, 3, 4, and 5 cm and/or at most about 10, 9, 8, 7, 6, and 5 cm (e.g., about 4-6 cm, about 1-5 cm, etc.). In some embodiments, for example, the flow channel comprises a width from about 1 mm to about 10 mm. In other embodiments, for instance, the flow channel comprises a width from about 3 mm to about 5 mm. In further embodiments, for example, the flow channel comprises a width of about 4 mm. As such, in certain embodiments, the flow channel comprises a width from at least about any of the following: 1, 2, 3, and 4 mm and/or at most about 10, 9, 8, 7, 6, 5, and 4 mm (e.g., about 2-6 mm, about 3-9 mm, etc.).

Figure 6A:
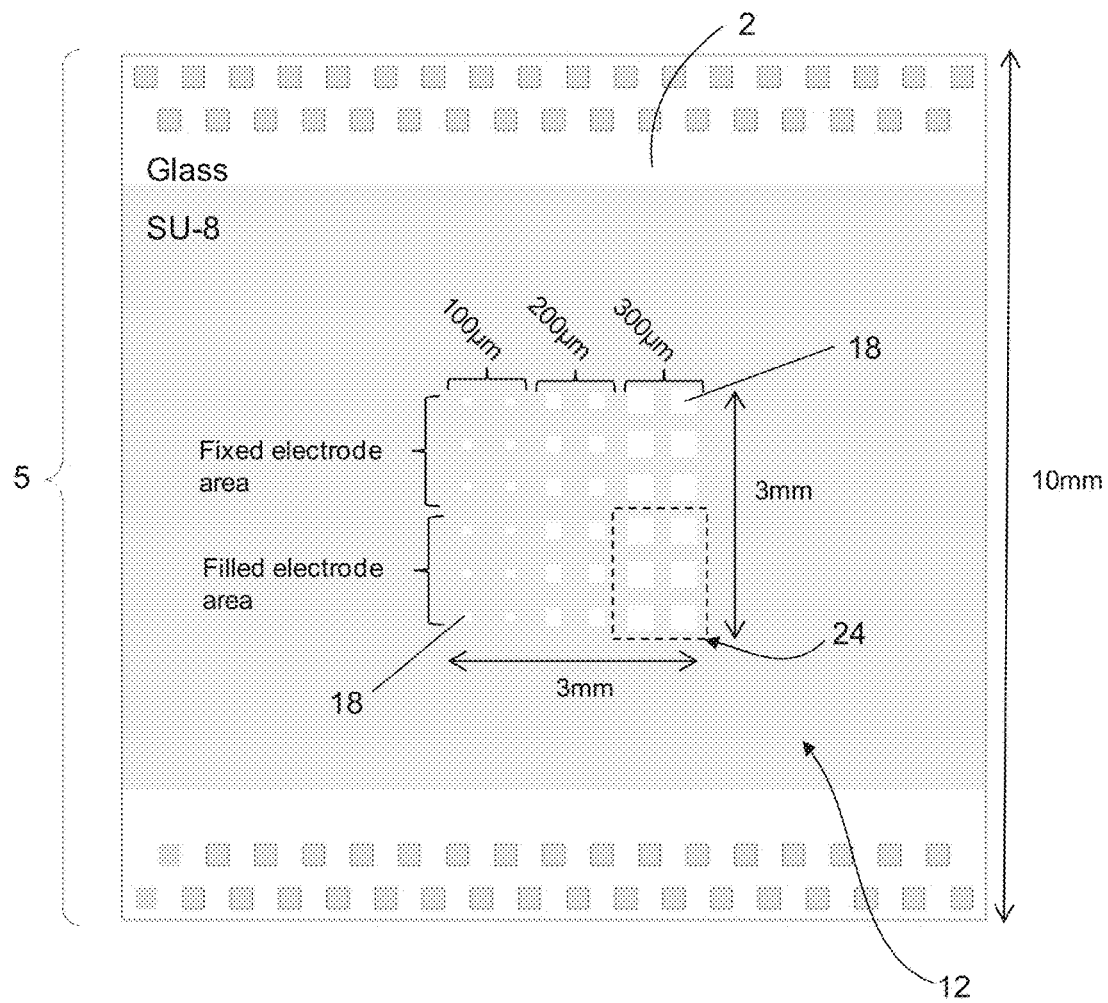
FIG. 6A illustrates a top view of an alternative layout for a multiplexed LC sensor array according to an example embodiment.

FIGS. 2A and 2B illustrate side views of LC sensor arrays according to example embodiments. For instance, FIG. 2A is a side view of FIG. 1A, and FIG. 2B is a side view of FIG. 1B. As illustrated by FIGS. 2A and 2B, regardless of whether a plurality of acrylic wells or flow channels are used to form the LC sensor array 5, the wells and/or flow channels contain the electrodes 18 on a sensor support surface 9 (e.g., a glass microscopic slide) with the LC 14 positioned above the electrodes 18 and a buffer/analyte solution 13 positioned above the LC 14. In FIG. 2B, the flow channel 4 includes a glass microscopic slide 9A positioned under the electrodes 18. The flow channel 4 also includes a glass microscopic slide 9B positioned above the electrodes 18. In this regard, the two glass microscopic slides 9A, 9B define the boundaries of the flow channel 4. As such, a sample may be input into inlet port 6, the sample may move in flow direction F through the flow channel 4, and the sample output may exit the flow channel 4 via the exit port 8. In some embodiments, the glass microscopic slide 9A and/or end portions of flow channel 4 may comprise a silane (e.g., polydimethylsiloxane (PDMS), dimethyloctadecyl[3-(trimethoxysilyl)propyl]ammonium chloride (DMOAP), etc.) coating 12 (as shown in FIG. 6A). In addition, the glass microscopic slides 9A, 9B may be spaced apart at the ends of the flow channel 4 via adhesive spacers 14.

As previously mentioned, the LC sensor array 5 may comprise a plurality of hexagonal wells 16. FIGS. 3A-3C, for example, illustrate varying magnifications of top views of an LC sensor array according to an example embodiment. As shown in FIGS. 3A-3C, an electrode is much larger than each well 16. For instance, as shown in FIG. 3A, the area occupied by all of the electrodes under the glass microscopic slide 9A, including a first electrode, may be from about 1 mm to about 5 mm wide, but as shown in FIGS. 3B and 3C, each well 16 may only be approximately 200-300 µm wide. In addition, as illustrated in FIGS. 3A-3C, the electrodes may be square, while the wells 16 may be hexagonal. However, these shapes are merely provided as examples, and each of the electrodes 18 and wells 16 may be any suitable shape for the applications described herein as understood by one of ordinary skill in the art.

Figure 6B:
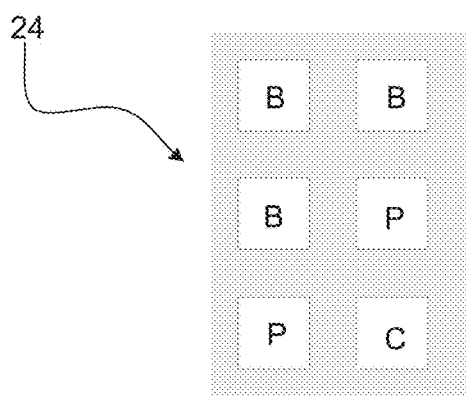
FIG. 6B illustrates the LC crystal and interdigitated electrode arrangement in dashed area 24 as shown in FIG. 6A according to an example embodiment.

FIG. 6A, for instance, illustrates a top view of an LC sensor array according to an example embodiment. As shown in FIG. 6A, the electrodes 18 may be configured in a pattern organized by fixed electrodes and filled electrodes within the LC sensor array 5. The electrode pattern is positioned in the portion of the glass microscopic slide 9A having the silane coating 12. FIG. 6B, for example, illustrates the electrode arrangement in dashed area 24 as shown in FIG. 6A according to an example embodiment. As shown in FIG. 6B, a sample pattern within dashed area 24 includes three butterfly electrodes, two parallel electrodes, and a control electrode, all within the filled electrode area.

In accordance with certain exemplary embodiments, for instance, the target biological agent may comprise at least one of a nucleic acid, a protein, a small molecule, or any combination thereof. In some embodiments, for example, the target biological agent may comprise a nucleic acid or a protein. In such embodiments, for instance, the capacitive LC biosensor may further comprise a nucleic acid extraction portion, the nucleic acid extraction portion being configured to extract nucleic acid from a sample to form an extracted nucleic acid, and a nucleic acid amplification portion, the nucleic acid amplification portion being configured to amplify the extracted nucleic acid for sensing via the LC biosensor. In addition, in further embodiments in which the target biological agent comprises a nucleic acid or a protein, for example, the analyte may comprise a single-stranded DNA molecule anchored to a cholesterol molecule. However, in other embodiments, for instance, the target biological agent may comprise a small molecule. In such embodiments, for example, the analyte may comprise a small molecule receptor anchored to a cholesterol molecule. In some embodiments, for instance, the small molecule receptor may comprise double-stranded DNA (dsDNA), a protein, RNA and/or the like.

According to certain embodiments, the target biological agent may comprise at least one of a virus, a bacterium, a prion, a toxin, an environmental hazard, a chemical, or any combination thereof. For example, the target biological agent may comprise a virus including, but not limited to, a flavivirus, an alphavirus, a bromovirus, an arterivirus, an aphthovirus, a rhinovirus, a hepatovirus, a cardiovirus, a cosavirus, a dicipivirus, an erbovirus, a kobuvirus, a megrivirus, a parechovirus, a piscevirus, a salivirus, a sapelovirus, a senecavirus, a teschovirus, a tremovirus, a potyvirus, a coronavirus, a norovirus, an orthomyxovirus, a rotavirus, a picobirnavirus, an enterovirus, a bymovirus, a comovirus, a nepovirus, a nodavirus, a picornavirus, a sobemovirus, a luteovirus, a carmovirus, a dianthovirus, a pestivirus, a tombusvirus, a bacteriophage, a carlavirus, a furovirus, a hordeivirus, a potexvirus, a rubivirus, a tobravirus, a tricornavirus, a tymovirus, and/or the like. In further embodiments, for example, the target biological agent may comprise a virus including, but not limited to, dengue virus (e.g., DENV1, DENV2, DENV3, DENV4), West Nile virus, absettarov virus, alkhurma virus, deer tick virus, gadgets gully virus, kadam virus, karshi virus, kyasanur forest disease virus, Langat virus, louping ill virus, omsk hemorrhagic fever virus, powassan virus, royal farm virus, sokuluk virus, tick-borne encephalitis virus, Turkish sheep encephalitis virus, kama virus, meaban virus, Saumarez Reef virus, tyuleniy virus, Aedes flavivirus, barkedji virus, calbertado virus, cell fusing agent virus, chaoyang virus, culex flavivirus, culex theileri flavivirus, donggang virus, ilomantsi virus, Kamiti River virus, lammi virus, marisma mosquito virus, nakiwogo virus, nhumirim virus, nounane virus, Spanish culex flavivirus, Spanish ochlerotatus flavivirus, quang binh virus, aroa virus, bussuquara virus, kedougou virus, cacipacore virus, koutango virus, ilheus virus, Japanese encephalitis virus, Murray Valley encephalitis virus, alfuy virus, rocio virus, St. Louis encephalitis virus, usutu virus, yaounde virus, kokobera virus, bagaza virus, baiyangdian virus, duck egg drop syndrome virus, Jiangsu virus, Israel turkey meningoencephalomyelitis virus, ntaya virus, tembusu virus, zika virus, banzi virus, bouboui virus, edge hill virus, jugra virus, saboya virus, sepik virus, Uganda S virus, wesselsbron virus, yellow fever virus, Entebbe bat virus, yokose virus, apoi virus, vowbone ridge virus, Jutiapa virus, modoc virus, sal vieja virus, san perlita virus, bukalasa bat virus, Carey Island virus, Dakar bat virus, Montana myotis leukoencephalitis virus, Phnom Penh bat virus, Rio Bravo virus, soybean cyst nematode virus 5, Aedes cinereus flavivirus, Aedes vexans flavivirus, Coxsackievirus, echovirus, Enterovirus A, Enterovirus B, Enterovirus C, Enterovirus D, Enterovirus E, Enterovirus F, Enterovirus G, Enterovirus H, Enterovirus J, Rhinovirus A, Rhinovirus B, Rhinovirus C, poliovirus, bovine viral diarrhea virus, sindbis virus, hepatitis C, Barmah Forest virus, eastern equine encephalitis virus, Middelburg virus, ndumu virus, bebaru virus, chikungunya virus, mayaro virus, una virus, o'nyong nyong virus, Igbo-Ora virus, Ross River virus, getah virus, sagiyama virus, Semliki Forest virus, me tri virus, cabassou virus, Everglades virus, mosso das pedras virus, mucambo virus, paramana virus, pixuna virus, Rio Negro virus, trocara virus, Bijou Bridge virus, Venezuelan equine encephalitis virus, aura virus, babanki virus, kyzylagach virus, ockelbo virus, whataroa virus, Buggy Creek virus, Fort Morgan virus, Highlands J virus, western equine encephalitis virus, salmon pancreatic disease virus, sleeping disease virus, southern elephant seal virus, tonate virus, Brome mosaic virus, equine arteritis virus, foot-and-mouth disease virus, bovine rhinitis A virus, bovine rhinitis B virus, equine rhinitis A virus, aquamavirus A, duck hepatitis A virus, encephalomyocarditis virus, theilovirus, cosavirus A, cadicivirus A, equine rhinitis B virus, hepatitis A virus, aichivirus A, aichivirus B, aichivirus C, melegrivirus A, human parechovirus, Ljungan virus, fathead minnow picornavirus, salivirus A, porcine sapelovirus, simian sapelovirus, avian sapelovirus, Seneca Valley virus, porcine teschovirus, avian encephalomyelitis virus, potato virus A, SARS, Human coronavirus 229E, Human coronavirus OC43, New Haven coronavirus, Human coronavirus HKU1, Middle East respiratory syndrome coronavirus, infectious bronchitis virus, porcine coronavirus, bovine coronavirus, feline coronavirus, canine coronavirus, turkey coronavirus, ferret enteric coronavirus, ferret systemic coronavirus, pantropic canine coronavirus, porcine epidemic diarrhea virus, Ebola virus, measles virus, Influenza virus A, Influenza virus B, Influenza virus C, isavirus, thogotovirus, quaranjavirus, Norwalk virus, Hawaii virus, Snow Mountain virus, Mexico virus, Desert Shield virus, Southampton virus, Lordsdale virus, Wilkinson virus, bluetongue virus, hepatitis E virus, apple chlorotic leaf spot virus, beet yellows virus, Rubella virus, Marburg virus, Mumps virus, Nipah virus, Hendra virus, RSV, NDV, Rabies virus, Nyavirus, Lassa virus, Hantavirus, Crimean-Congo hemorrhagic fever, hepatitis D virus, Nyamanini virus, Midway virus, and/or the like.

In other embodiments, for instance, the target biological agent may comprise a bacterium including, but not limited to, *Salmonella typhi, Rickettsia prowazekii, Rickettsia typhi, Orientia tsutsugamushi, Rickettsia australis, Streptococcus pneumonia, Haemophilus influenza, Streptococcus pyogenes, Neisseria meningitides, Bacillus anthracis, Clostridium tetani, Mycobacterium tuberculosis, Mycobacterium bovis, Bordetella pertussis, Vibrio cholera, Corynebacterium diphtheria, Clostridium botulinum*, and/or the like.

In further embodiments, for example, the target biological agent may comprise a prion including, but not limited to, scrapie, bovine spongiform encephalopathy, transmissible mink encephalopathy, chronic wasting disease, feline spongiform encephalopathy, exotic ungulate encephalopathy, spongiform encephalopathy, Creutzfeldt-Jakob disease, Gerstmann-Sträussler-Scheinker syndrome, fatal familial insomnia, kuru, multiple system atrophy, and/or the like.

In some embodiments, for instance, the target biological agent may comprise a toxin including, but not limited to, a venom, a poison, any other biotoxin and/or the like. For example, the venom may comprise venom derived from spiders, centipedes, scorpions, stinging insects (e.g., bees, wasps, etc.), caterpillars, ants, true bugs, jellyfish (e.g., box jellyfish), cone snails, coleoids, cartilaginous fish (e.g., stingrays, sharks, chimaeras, etc.), teleost fish (e.g., onejaws, catfish, stonefish, waspfish, scorpionfish, lionfish, etc.), salamandrid salamanders, snakes, Mexican beaded lizards, gila monsters, monitor lizards, Komodo dragons, solenodons, shrews, platypi, and/or the like.

In other embodiments, for instance, the target biological agent may comprise an environmental hazard including, but not limited to, air pollutants, organophosphate pesticides and/or the like. In further embodiments, for example, the target biological agent may comprise a chemical including, but not limited to, simulants of nerve agents, toxic industrial chemicals, chemical warfare agents, pharmaceutical agents and/or the like.

III. Capacitive LC Biosensor Device

In another aspect, certain exemplary embodiments provide a capacitive liquid crystal (LC) biosensor device. For instance, this device provides a lightweight, portable, cost-effective platform for identifying a target biological agent(s) based on, for example, nucleic acid, proteins, and small molecules. According to certain embodiments, the device may include an exterior portion comprising a display and an interior portion comprising a capacitive LC biosensor, a sample input portion upstream of the capacitive LC biosensor, and a wicking cap downstream of both the sample input portion and the capacitive LC biosensor. For example, the capacitive LC biosensor may comprise a support board; at least one of a flow channel or a plurality of acrylic wells positioned on the support board, the flow channel having an inlet port positioned at a first end and an exit port positioned at a second end; at least two electrodes, the at least two electrodes comprising a first electrode disposed on a flow channel first surface and a second electrode disposed on a flow channel second surface opposite the flow channel first surface; an electricity source connected to the first electrode and the second electrode; and an LC sensor array positioned within the flow channel. The LC sensor array, for example, may comprise a sensor support surface; a plurality of hexagonal wells positioned on the sensor support surface; an organic LC phase positioned within each of the plurality of wells; and an aqueous phase comprising an analyte positioned above the organic LC phase within the plurality of wells. According to certain exemplary embodiments, for instance, the plurality of hexagonal wells may comprise an epoxy-based negative photoresist (i.e. SU-8) formulated via photolithography.

Figure 4B:
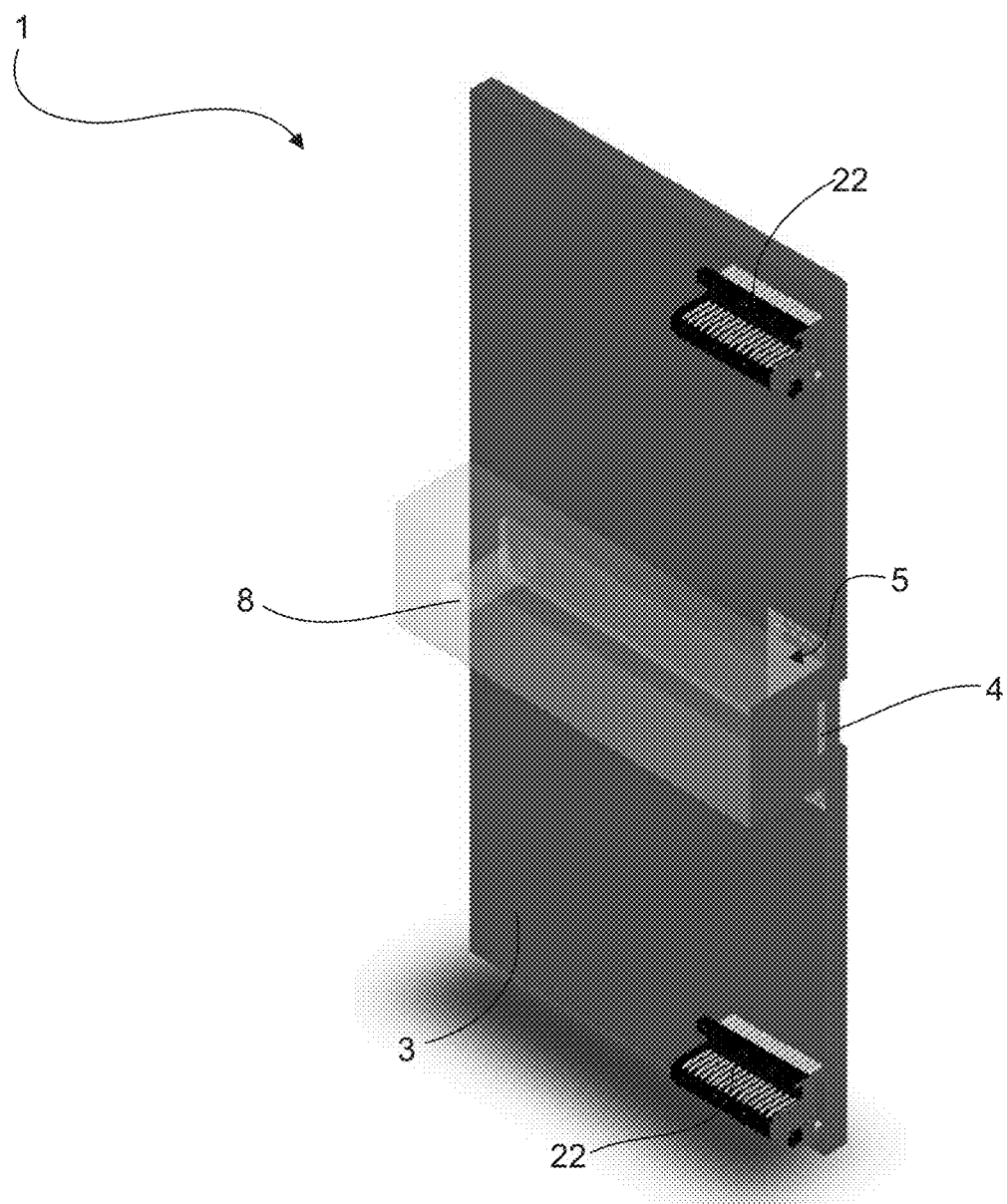
FIG. 4B illustrates a cutaway perspective view of a capacitive LC biosensor that includes on board electronics according to an example embodiment.
Figure 5:
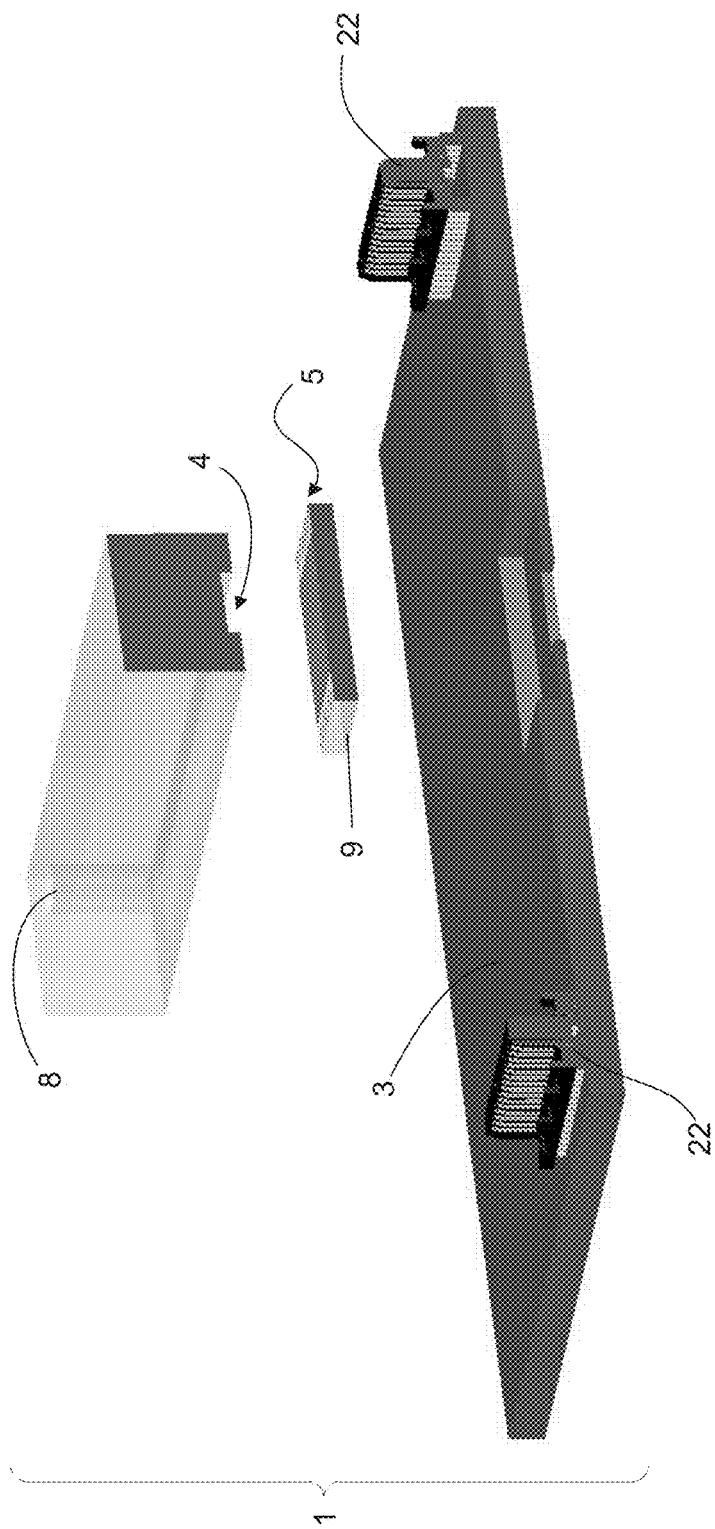
FIG. 5 illustrates an exploded perspective view of a capacitive LC biosensor that includes on board electronics according to an example embodiment.

In accordance with certain exemplary embodiments, for instance, the device may be paper-based. In further embodiments, for example, the device may operate via passive lateral flow. In some embodiments, for instance, the capacitive LC biosensor may further comprise at least two instrumentation connectors for connecting to the exterior portion of the device. FIGS. 4A, 4B, and 5 illustrate various perspective views of a capacitive LC biosensor as used in a capacitive LC biosensor device according to example embodiments. For example, FIG. 4A illustrates a perspective view of a capacitive LC biosensor device according to an example embodiment, FIG. 4B illustrates a cutaway perspective view of a capacitive LC biosensor according to an example embodiment, and FIG. 5 illustrates an exploded perspective view of a capacitive LC biosensor according to an example embodiment. Each of FIGS. 4A, 4B, and 5 show the aspects of the capacitive LC biosensor 1 that have been discussed above in addition to the instrumentation connectors 22 that are configured to connect the capacitive LC biosensor 1 to the device 26.

Figure 7A:
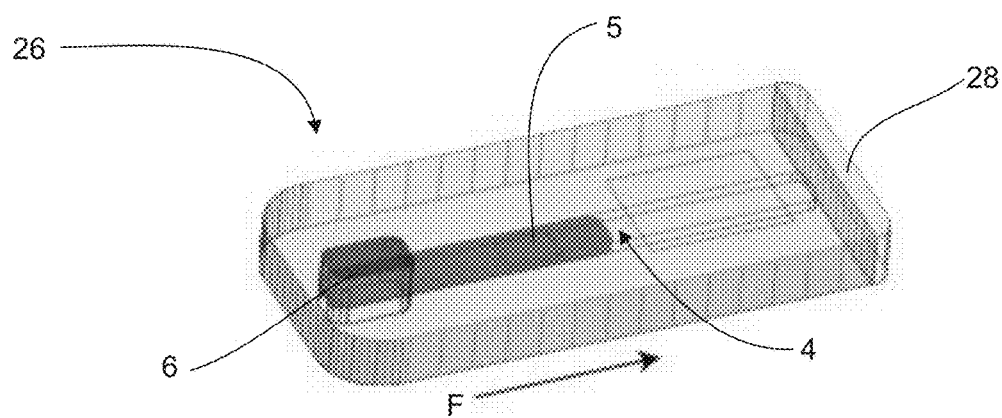
FIGS. 7A and 7B illustrate perspective and top/side views of a disposable, portable biosensor with sensing mechanism based on an LC sensor array according to an example embodiment.
Figure 7B:
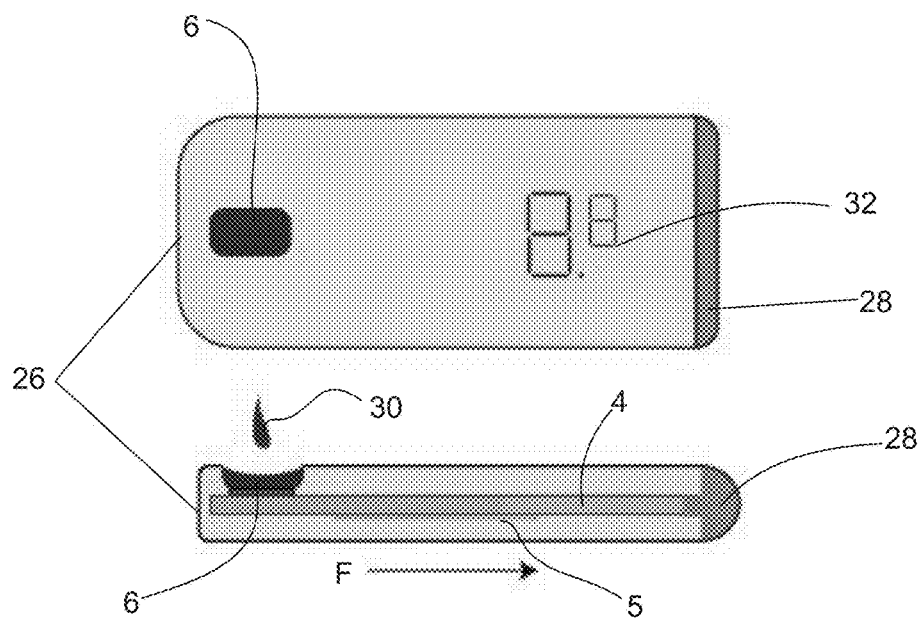

FIGS. 7A and 7B, for example, illustrate a capacitive LC biosensor device according to an example embodiment. As shown in FIGS. 7A and 7B, the device 26 includes an interior portion having the inlet port 6 of the flow channel 4, the LC sensor array 5, and a wicking cap 28. The wicking cap 28 causes the sample 30 to move through the flow channel 4 in the flow direction F via passive lateral flow and may also serve as a waste container for the used sample. The device 26 may require approximately 20 µL of sample 30 per electrode 18. The device 26 also includes an exterior portion having a display 32 and the inlet port 6 for input of the sample 30. In this regard, the device 26 provides a simple readout for a user on the display 32 after processing the sample 30. As such, the device 26 may have a sensitivity of about 1 nM and may be selective to 1 base pair MM.

IV. Method for Sensing a Target Biological Agent

In yet another aspect, certain exemplary embodiments provide a method for sensing a target biological agent. For instance, this method provides for the operation of a lightweight, portable, cost-effective platform for identifying a target biological agent(s) based on, for example, nucleic acid, proteins, and small molecules. According to certain embodiments, the method may include providing a capacitive LC biosensor, adding a sample to the capacitive LC biosensor, and identifying whether a state change occurred in association with adding the sample to the capacitive LC biosensor in order to determine whether the target biological agent is present in the sample. The state change may occur in association with adding a sample containing a complementary target biological agent, while no state change may occur if the sample does not contain any complementary target biological agents. In this regard, the state change may occur in response to the change in capacitance that occurs with a change in liquid crystal orientation upon DNA hybridization.

In certain exemplary embodiments, for instance, the method may further comprise multiplexing the method in order to generate readable barcodes from an array of positive and negative sample responses. In this regard, the capacitive LC biosensor and methods of operating thereof will significantly enhance the development of multiplex detection formats to enable the interrogation of a sample for the presence of multiple organisms or targets simultaneously. As such, for example, the methods and devices may permit interrogation and identification of pathogens and/or contaminants at sample collection sites, thereby limiting the need to ship samples to laboratories and, as a result, providing rapid readouts, thereby permitting faster identification of pathogens and/or contaminants in urgent situations (e.g., disease outbreak, environmental crisis, etc.) against a variety of agents.

Figure 8:
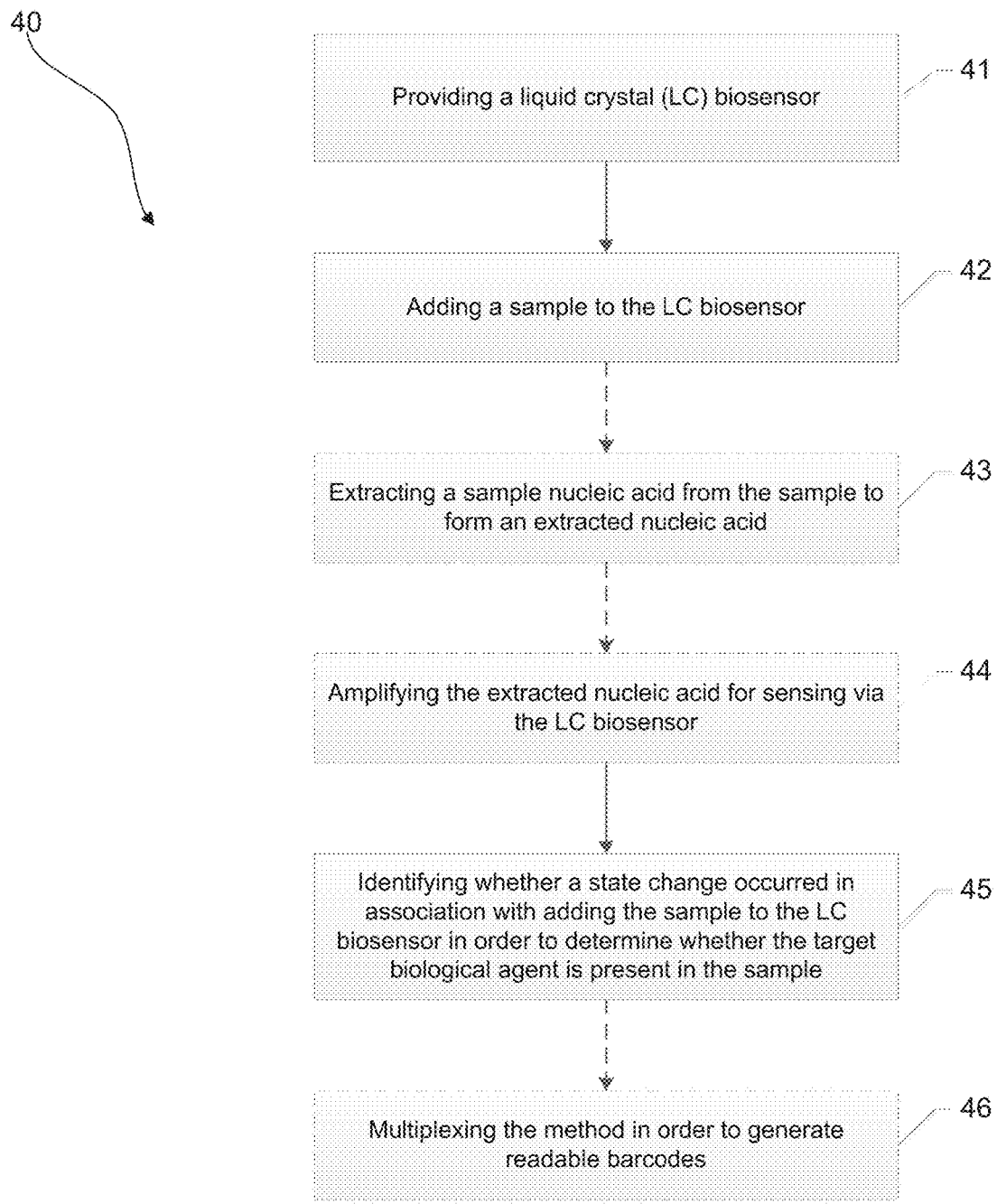
FIG. 8 illustrates a block diagram of a method for sensing a target biological agent including the optional steps of extracting a sample nucleic acid from the sample to form an extracted nucleic acid, amplifying the extracted nucleic acid for sensing via the LC biosensor, and multiplexing the method in order to generate readable barcodes according to an example embodiment.

FIG. 8, for example, illustrates a block diagram of a method for sensing a target biological agent including the optional steps of extracting a sample nucleic acid from the sample to form an extracted nucleic acid, amplifying the extracted nucleic acid for sensing via the LC biosensor, and multiplexing the method in order to generate readable barcodes according to an example embodiment. As shown in FIG. 8, the method 40 includes providing a liquid crystal (LC) biosensor at operation 41, adding a sample to the LC biosensor at operation 42, optionally extracting a sample nucleic acid from the sample to form an extracted nucleic acid at operation 43, optionally amplifying the extracted nucleic acid for sensing via the LC biosensor at operation 44, identifying whether a state change occurred in association with adding the sample the LC biosensor in order to determine whether the target biological agent is present in the sample at operation 45, and optionally multiplexing the method 40 in order to generate readable barcodes at operation 46.

Figure 9:
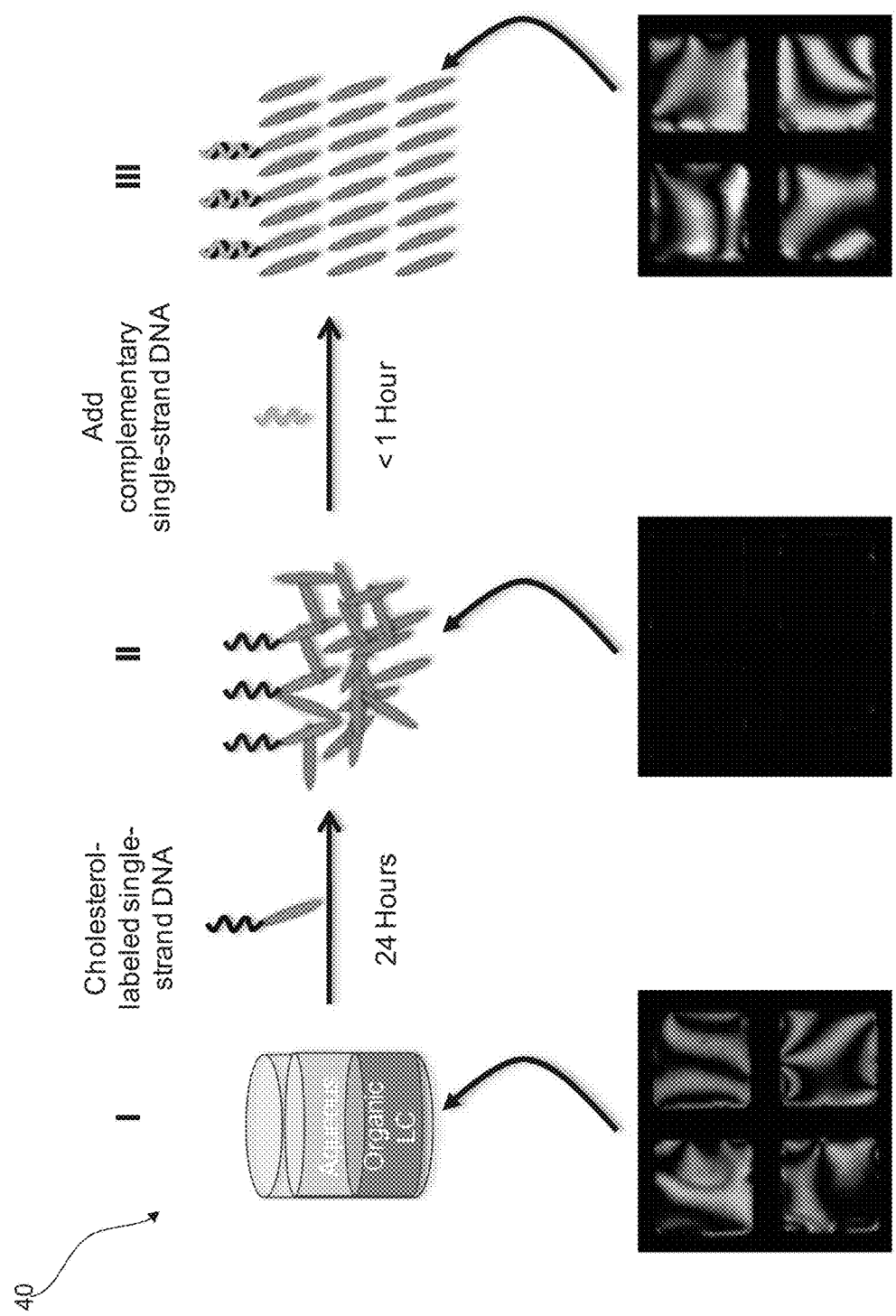
FIG. 9 illustrates an overview of a method for sensing a target biological agent according to an example embodiment.
Figure 10:
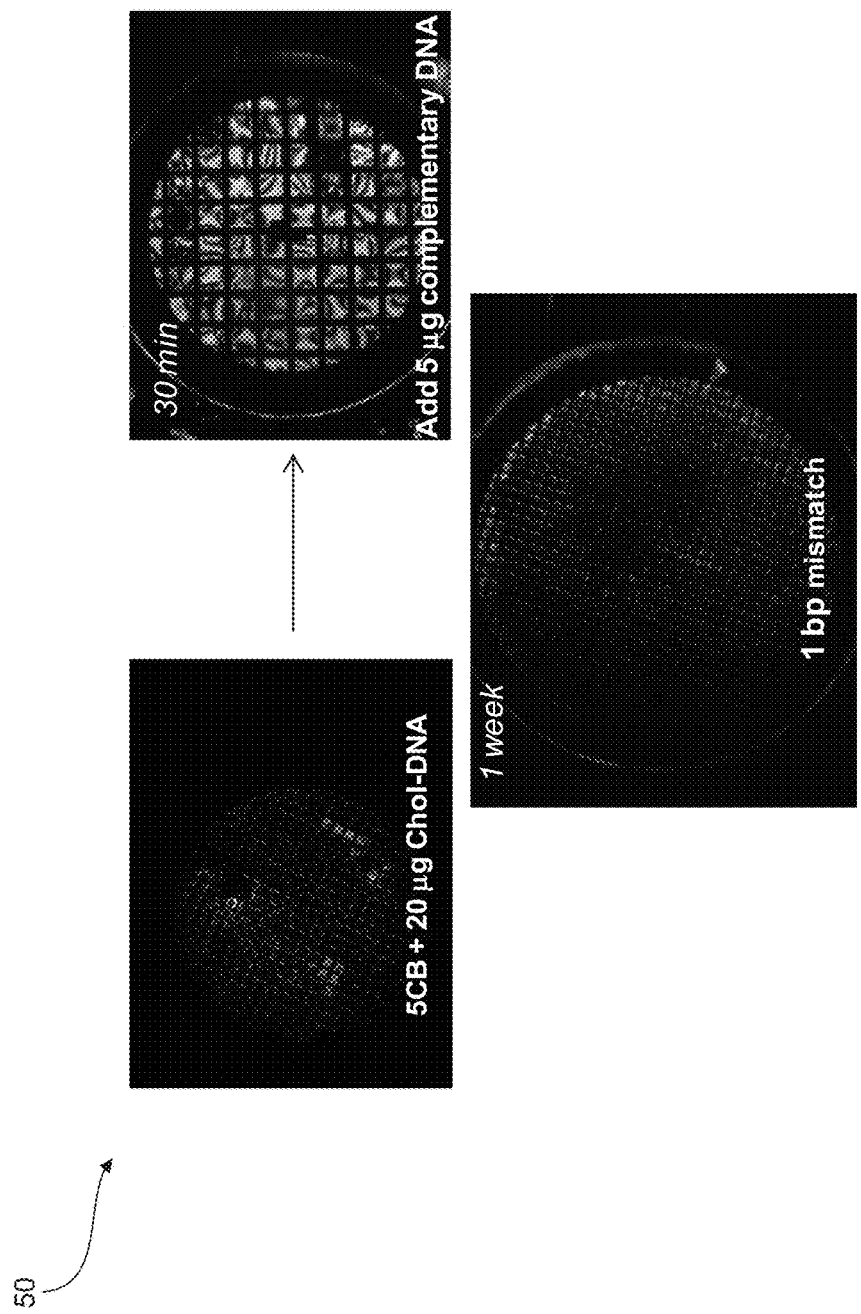
FIG. 10 illustrates the optical effects of a single base pair mismatch, which corresponds to a capacitive LC biosensor response according to an example embodiment.

FIG. 9, for instance, illustrates an overview of a method for sensing a target biological agent according to an example embodiment. As shown in FIG. 9, the method 40 includes providing an LC biosensor having an aqueous phase positioned above an organic LC phase within a well such that the liquid crystals exhibit birefringence, adding cholesterol-labeled ssDNA to the well such that after 24 hours the liquid crystals no longer exhibit birefringence, and adding a sample such that if the sample contains the target biological agent, the liquid crystals will become ordered and exhibit birefringence within an hour due to DNA hybridization. FIG. 10, for example, illustrates the effects of a single base pair mismatch on the capacitive LC biosensor response according to an example embodiment. As shown in FIG. 10, even a single base pair mismatch will prevent birefringence over time. Specifically, the liquid crystals may initially display some birefringence after about thirty minutes after adding complementary DNA having one base pair mismatch, but after one week, the single base pair mismatch will cause the liquid crystals to stop exhibiting birefringence.

In accordance with certain exemplary embodiments, for instance, providing the capacitive LC biosensor may comprise providing the capacitive LC biosensor to include a support board; a flow channel positioned on the support board, the flow channel having an inlet port positioned at a first end and an exit port positioned at a second end; at least two electrodes, the at least two electrodes comprising a first electrode disposed on a flow channel first surface and a second electrode disposed on a flow channel second surface opposite the flow channel first surface; an electricity source connected to the first electrode and the second electrode; and an LC sensor array positioned within the flow channel. The LC sensor array, for example, may comprise a sensor support surface; a plurality of wells positioned on the sensor support surface; an organic LC phase positioned within each of the plurality of wells; and an aqueous phase comprising an analyte positioned above the organic LC phase within the plurality of wells. According to certain exemplary embodiments, for instance, the plurality of wells may comprise an epoxy-based negative photoresist (i.e. SU-8) formulated via photolithography.

In accordance with certain exemplary embodiments, for instance, the first and second electrodes may comprise gold electrodes. In some embodiments, for example, at least one of the first and second electrodes may comprise a gold interdigitated electrode.

In accordance with certain exemplary embodiments, for instance, the target biological agent may comprise at least one of a nucleic acid, a protein, a small molecule, or any combination thereof. In some embodiments, for example, the target biological agent may comprise a nucleic acid or a protein.

In further embodiments, for instance, prior to identifying whether a state change occurred in association with adding the sample to the capacitive LC biosensor in order to determine whether the target biological agent is present in the sample, the method may further comprise extracting a sample nucleic acid from the sample to form an extracted nucleic acid and amplifying the extracted nucleic acid for sensing via the capacitive LC biosensor. In such embodiments, for example, extracting the nucleic acid from the sample to form the extracted nucleic acid may comprise lysing the biological agent in the sample to form a lysed biological agent, and extracting, by way of example only, RNA from the lysed biological agent to form extracted RNA. For instance, RNA may be extracted by any suitable extraction method that is compatible with the methods and devices discussed herein as understood by one of ordinary skill in the art. In this regard, the sample extraction and preparation may be integrated into the methods and devices disclosed herein. In accordance with certain exemplary embodiments, for instance, amplifying the extracted nucleic acid to form the nucleic acid amplicon may comprise isothermally amplifying the extracted nucleic acid. In further embodiments, for example, isothermally amplifying the extracted nucleic acid may comprise performing nucleic acid sequence-based amplification (NASBA) on the extracted nucleic acid. Using RNA as an example, the NASBA procedure may comprise synthesizing an RNA strand from a template RNA strand utilizing a first strand synthesis primer and avian myeloblastosis virus reverse transcriptase (AMV-RT). Next, the template RNA strand may be cleaved using RNase H. A second RNA strand may then be synthesized utilizing a second strand synthesis primer and AMV-RT. Finally, the cRNA amplicon may be synthesized from the two RNA strands by using T7 RNA polymerase. By utilizing a nucleic acid amplification step, the assay sensitivity and specificity may be significantly enhanced.

In accordance with certain exemplary embodiments, for instance, the method may further comprise performing size exclusion chromatography or other selective binding between extracting the nucleic acid and amplifying the extracted nucleic acid, and amplifying the extracted nucleic acid and tagging the nucleic acid amplicon. In this regard, the size exclusion chromatography may act as manual gates between each of the steps to only allow the molecules of interest through to the next step.

In some embodiments in which the target biological agent comprises a nucleic acid or a protein, for example, identifying whether a state change occurred in association with adding the sample to the capacitive LC biosensor may comprise capacitively sensing DNA hybridization. In addition, in further embodiments in which the target biological agent comprises a nucleic acid or a protein, for instance, the analyte may comprise a single-stranded DNA molecule anchored to a cholesterol molecule. However, in other embodiments, for example, the target biological agent may comprise a small molecule. In such embodiments, for instance, the analyte may comprise a small molecule receptor anchored to a cholesterol molecule.

V. Examples

The present disclosure is further illustrated by the following examples, which in no way should be construed as being limiting. That is, the specific features described in the following examples are merely illustrative and not limiting.

Example 1

In Example 1, the effects of a ratio of cholesterol-tagged single-stranded DNA (ssDNA) to complementary sample ssDNA were measured. Liquid crystals (LC) were contained in lithographically-defined photoresist hexagonal wells with underlying square/diamond interdigitated electrode pads being visible through the hexagonal wells at room temperature (i.e. about 21° C.) and ambient humidity. The underlying glass/electrode surface was pretreated with a silane layer. Larger, acrylic wells containing an aqueous buffer (e.g., standard DNA hybridization buffer) were positioned on top of the hexagonal wells. The aqueous buffer and the LC formed an LC-buffer interface such that details of the LC-buffer interface defined the orientation of the LC and therefore the appearance of the LC between crossed polarizers used for imaging such that a birefringent LC (i.e. 5CB) appeared bright.

Figure 11A:
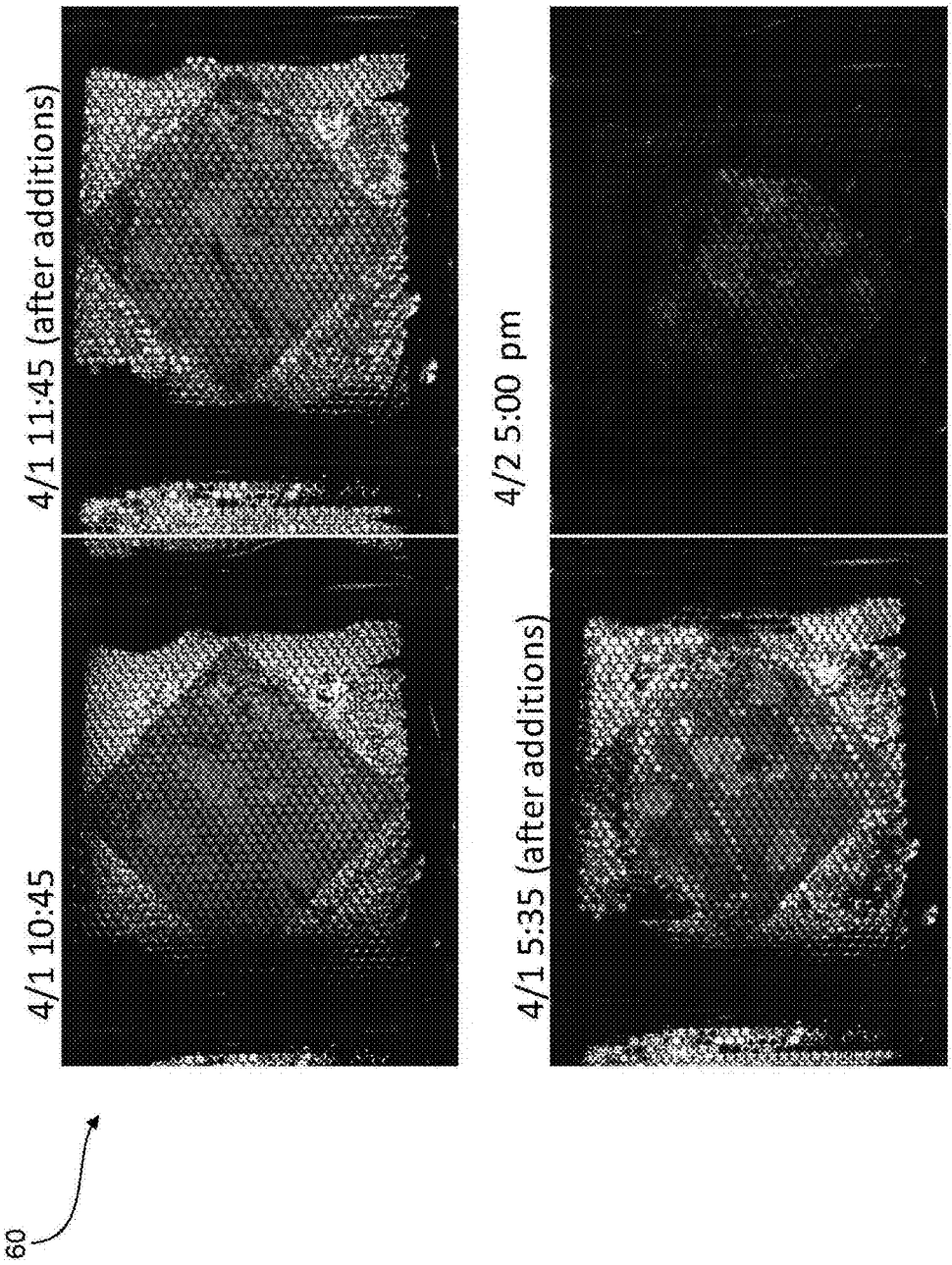
FIGS. 11A and 11B illustrate capacitive LC biosensor responses for varying test conditions according to example embodiments.

The top left image of FIG. 11A illustrates the addition of the LC and the aqueous DNA hybridization buffer. Cholesterol-labeled single-stranded DNA (ssDNA) was then added to the capacitive LC biosensor, producing an image shown in the top right image of FIG. 11A. Next, complementary sample ssDNA was added at a 1:1 ratio to match the cholesterol-labeled ssDNA, as imaged in the bottom left image of FIG. 11A. However, after approximately 24 hours, the LC orientation had evolved, as illustrated by the bottom right image of FIG. 11A. As such, FIG. 11A illustrates that the sample ssDNA bound with the cholesterol-labeled ssDNA.

Example 2

Figure 11B:
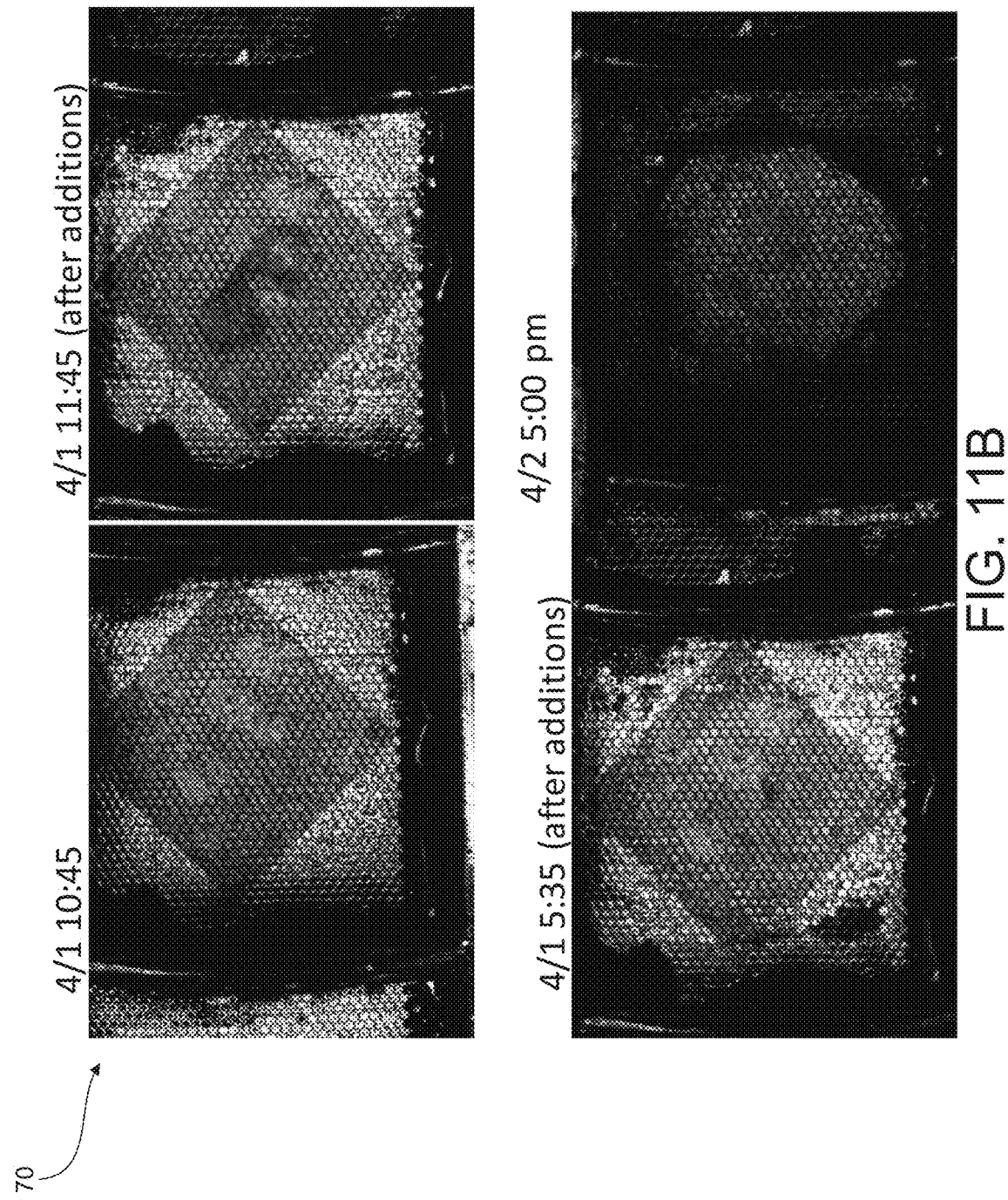

In Example 2, the effects of a ratio of cholesterol-tagged single-stranded DNA (ssDNA) to complementary sample ssDNA were measured. The capacitive LC biosensor and LC sensor array were prepared according to Example 1. However, the complementary sample ssDNA was added at a 1:2 ratio of cholesterol-labeled ssDNA to complementary sample ssDNA, producing the images shown in FIG. 11B. As shown in FIG. 11B, the LC demonstrated more birefringence after 24 hours of LC orientation evolution than the LC from Example 1 (and FIG. 11A).

Figure 12:
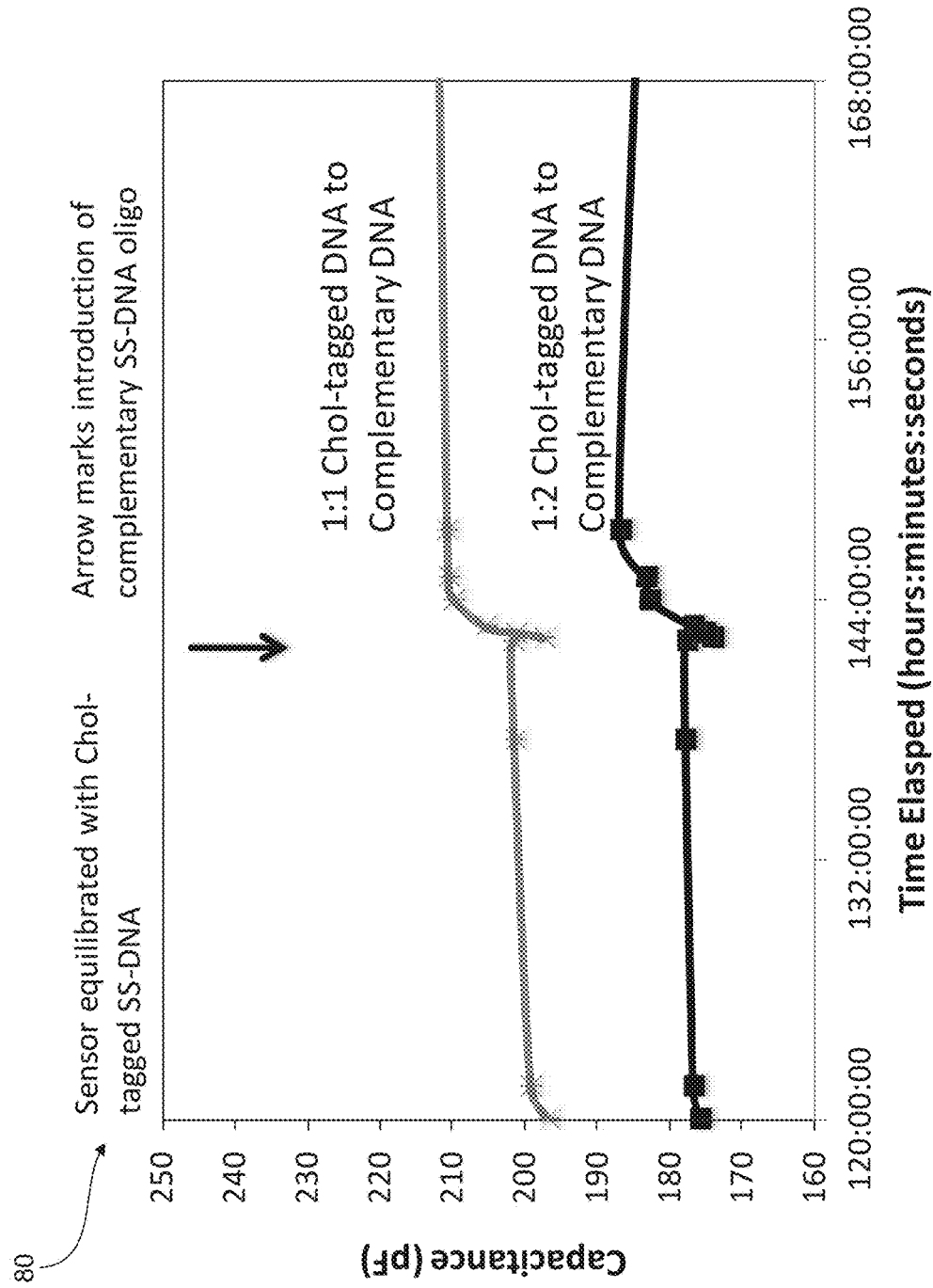
FIG. 12 illustrates the capacitive response of the capacitive LC biosensor to addition of complementary DNA according to example embodiments.

FIG. 12 illustrates the capacitive response of the capacitive LC biosensor to addition of complementary DNA according to Examples 1 and 2. Capacitance values were interrogated using an Ander-Hagerling 2700A capacitance bridge at 0.1V and 8 Hz via electrical connections that were made via gold leads outside of the well containing the LC and aqueous buffer. As shown in FIG. 12, when a complementary ssDNA oligomer was added to the capacitive LC biosensor equilibrated with the cholesterol-labeled ssDNA, the capacitance of the liquid crystals initially decreases but then rapidly increases, thereby indicating a state change in the electrical signals produced by the liquid crystals upon DNA hybridization. Additionally, the capacitance values illustrated in FIG. 12 confirm the optical tests performed in Examples 1 and 2 by illustrating that the ratio of cholesterol-tagged ssDNA to complementary sample ssDNA in Example 1 produced higher capacitance than the ratio of Example 2.

Example 3

Figure 13A:
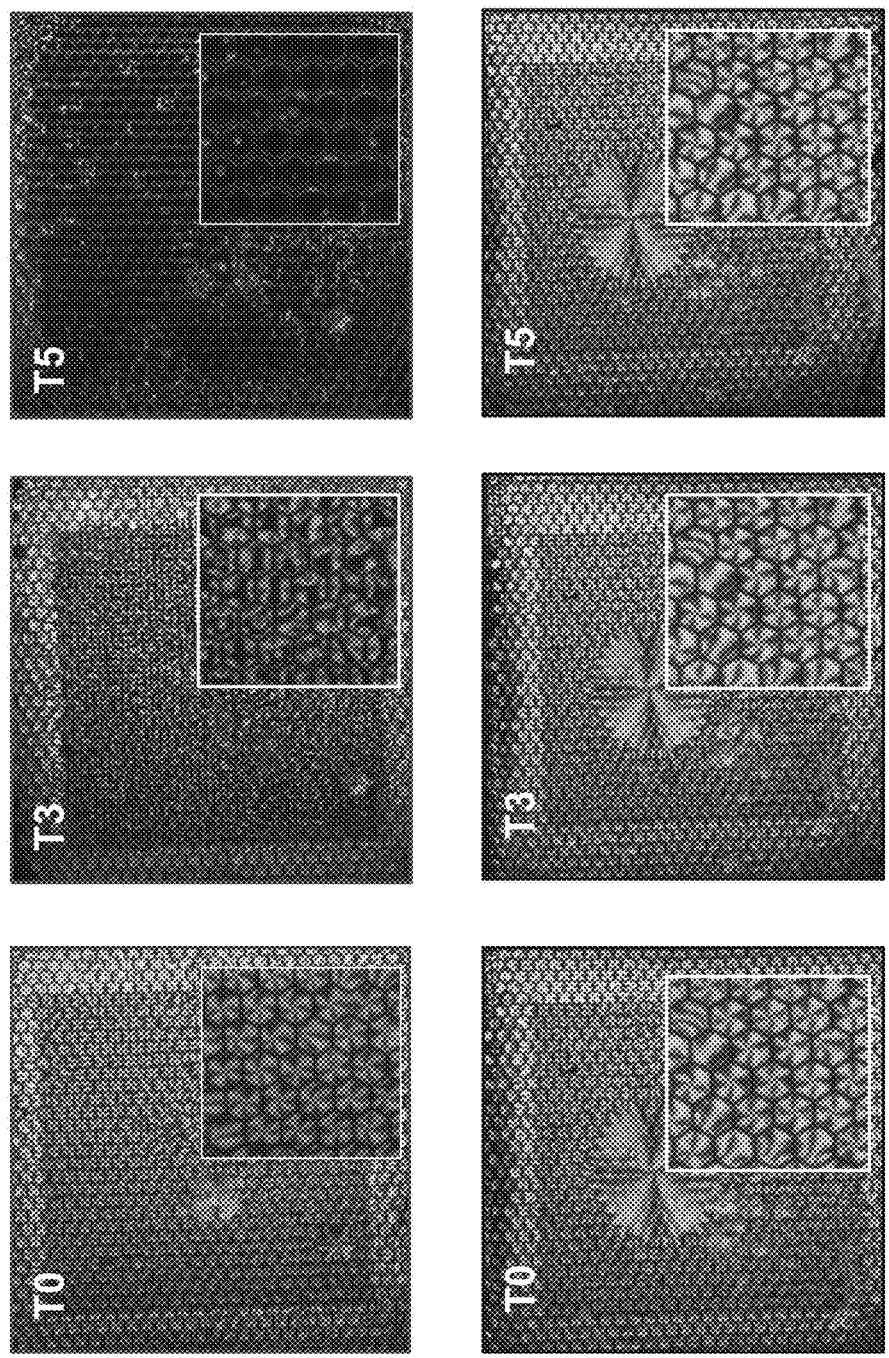
FIG. 13A illustrates the optical response of the capacitive LC biosensor to addition of a surfactant versus addition of a control buffer over time according to an example embodiment.
Figure 13B:
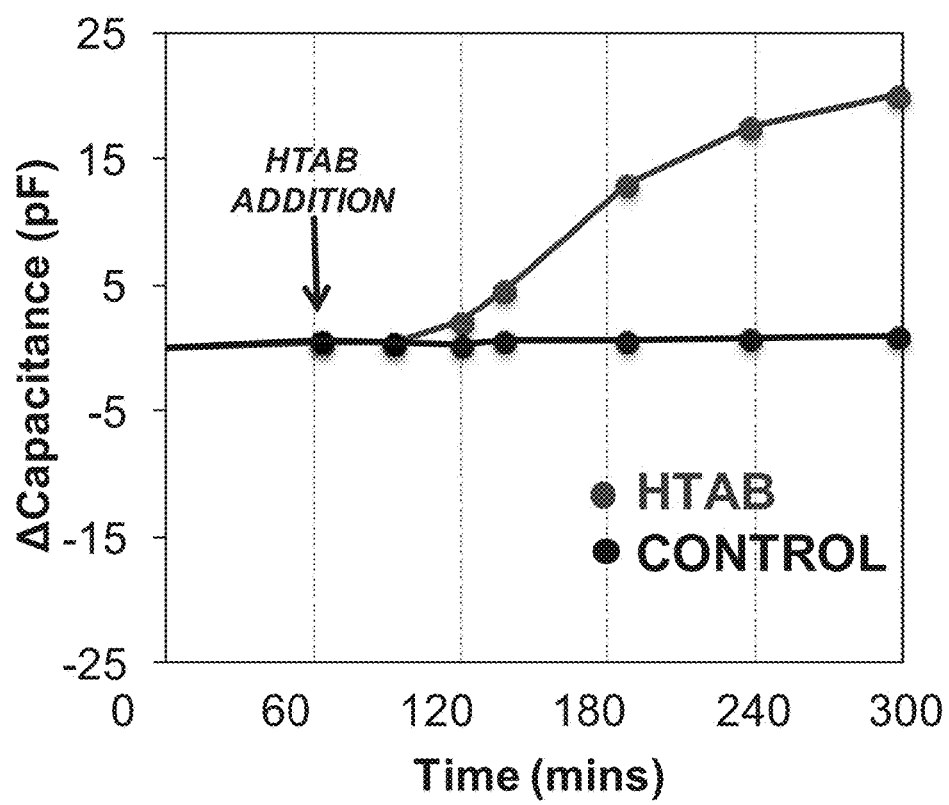
FIG. 13B illustrates the capacitive response of the capacitive LC biosensor to addition of a surfactant versus addition of a control buffer over time according to an example embodiment.

In Example 3, the effects of surfactant addition were measured. The capacitive LC biosensor and LC sensor array were prepared according to Example 1 with the exception that the aqueous buffer was deionized water. Both the top left and bottom left images of FIG. 13A illustrate the LC appearance of the LC and deionized water. Next, hexadecyltrimethylammonium bromide (HTAB) was added to one capacitive LC biosensor, while more deionized water was added to a second capacitive LC biosensor. The top middle image of FIG. 13A illustrates the change in LC orientation from the HTAB addition, while the bottom middle image illustrates no change in the LC orientation having the deionized water addition. After continued incubation, the top right image of FIG. 13A illustrates the lack of birefringence due to the addition of HTAB, while the bottom right image illustrates no change in the LC orientation due to the addition of deionized water. As such, the top images demonstrate that the surfactant HTAB affected the orientation of the LC over time. Similarly, FIG. 13B illustrates the change in capacitance created by the addition of HTAB to the capacitive LC biosensor as compared the stable capacitance of the control.

EXEMPLARY EMBODIMENTS

Certain exemplary embodiments provide a capacitive liquid crystal (LC) biosensor for sensing a target biological agent. For instance, this capacitive LC biosensor provides a lightweight, portable, cost-effective platform for identifying a target biological agent(s) based on, for example, nucleic acid, proteins, and small molecules. In one aspect, the capacitive LC biosensor includes a support board; a flow channel positioned on the support board, the flow channel having an inlet port positioned at a first end and an exit port positioned at a second end; at least two electrodes, the at least two electrodes comprising a first electrode disposed on a flow channel first surface and a second electrode disposed on a flow channel second surface opposite the flow channel first surface; an electricity source connected to the first electrode and the second electrode; and an LC sensor array positioned within the flow channel. The LC sensor array comprises a sensor support surface; a plurality of wells positioned on the sensor support surface; an organic LC phase positioned within each of the plurality of wells; and an aqueous phase comprising an analyte positioned above the organic LC phase within the plurality of wells.

In accordance with certain exemplary embodiments, the first and second electrodes comprise gold electrodes. In some embodiments, at least one of the first and second electrodes comprises a gold interdigitated electrode.

In accordance with certain exemplary embodiments, the target biological agent comprises at least one of a nucleic acid, a protein, a small molecule, or any combination thereof. In some embodiments, the target biological agent comprises a nucleic acid or a protein. In such embodiments, the capacitive LC biosensor further comprises a nucleic acid extraction portion, the nucleic acid extraction portion being configured to extract nucleic acid from a sample to form an extracted nucleic acid, and a nucleic acid amplification portion, the nucleic acid amplification portion being configured to amplify the extracted nucleic acid for sensing via the LC biosensor. In addition, in further embodiments in which the target biological agent comprises a nucleic acid or a protein, the analyte comprises a single-stranded DNA molecule anchored to a cholesterol molecule. However, in other embodiments, the target biological agent comprises a small molecule. In such embodiments, the analyte comprises a small molecule receptor anchored to a cholesterol molecule.

In another aspect, certain exemplary embodiments provide a capacitive liquid crystal (LC) biosensor device. For instance, this device provides a lightweight, portable, cost-effective platform for identifying a target biological agent(s) based on, for example, nucleic acid, proteins, and small molecules. According to certain embodiments, the device includes an exterior portion comprising a display and an interior portion comprising a capacitive LC biosensor, a sample input portion upstream of the capacitive LC biosensor, and a wicking cap downstream of both the sample input portion and the capacitive LC biosensor. The capacitive LC biosensor comprises a support board; a flow channel positioned on the support board, the flow channel having an inlet port positioned at a first end and an exit port positioned at a second end; at least two electrodes, the at least two electrodes comprising a first electrode disposed on a flow channel first surface and a second electrode disposed on a flow channel second surface opposite the flow channel first surface; an electricity source connected to the first electrode and the second electrode; and an LC sensor array positioned within the flow channel. The LC sensor array may comprise a sensor support surface; a plurality of wells positioned on the sensor support surface; an organic LC phase positioned within each of the plurality of wells; and an aqueous phase comprising an analyte positioned above the organic LC phase within the plurality of wells.

In accordance with certain exemplary embodiments, the device is paper-based. In further embodiments, the device operates via passive lateral flow. In some embodiments, the capacitive LC biosensor further comprises at least two instrumentation connectors for connecting to the exterior portion of the device.

In yet another aspect, certain exemplary embodiments provide a method for sensing a target biological agent. For instance, this method provides for operation of a lightweight, portable, cost-effective platform for identifying a target biological agent(s) based on, for example, nucleic acid, proteins, and small molecules. According to certain embodiments, the method includes providing a capacitive LC biosensor, adding a sample to the capacitive LC biosensor, and identifying whether a state change occurred in association with adding the sample to the capacitive LC biosensor in order to determine whether the target biological agent is present in the sample. In certain exemplary embodiments, the method further comprises multiplexing the method in order to generate readable barcodes.

In accordance with certain exemplary embodiments, providing the capacitive LC biosensor comprises providing the capacitive LC biosensor to include a support board; a flow channel positioned on the support board, the flow channel having an inlet port positioned at a first end and an exit port positioned at a second end; at least two electrodes, the at least two electrodes comprising a first electrode disposed on a flow channel first surface and a second electrode disposed on a flow channel second surface opposite the flow channel first surface; an electricity source connected to the first electrode and the second electrode; and an LC sensor array positioned within the flow channel. The LC sensor array comprises a sensor support surface; a plurality of wells positioned on the sensor support surface; an organic LC phase positioned within each of the plurality of wells; and an aqueous phase comprising an analyte positioned above the organic LC phase within the plurality of wells.

In accordance with certain exemplary embodiments, the first and second electrodes comprise gold electrodes. In some embodiments, at least one of the first and second electrodes comprises a gold interdigitated electrode.

In accordance with certain exemplary embodiments, the target biological agent comprises at least one of a nucleic acid, a protein, a small molecule, or any combination thereof. In some embodiments, the target biological agent comprises a nucleic acid or a protein. In further embodiments, prior to identifying whether a state change occurred in association with adding the sample to the capacitive LC biosensor in order to determine whether the garget biological agent is present in the sample, the method further comprises extracting a sample nucleic acid from the sample to form an extracted nucleic acid and amplifying the extracted nucleic acid for sensing via the capacitive LC biosensor. In some embodiments in which the target biological agent comprises a nucleic acid or a protein, identifying whether a state change occurred in association with adding the sample to the capacitive LC biosensor comprises capacitively sensing DNA hybridization. In addition, in further embodiments in which the target biological agent comprises a nucleic acid or a protein, the analyte comprises a single-stranded DNA molecule anchored to a cholesterol molecule. However, in other embodiments, the target biological agent comprises a small molecule. In such embodiments, the analyte comprises a small molecule receptor anchored to a cholesterol molecule.

Many modifications and other embodiments will come to mind to one skilled in the art to which this disclosure pertains having the benefit of the teachings presented in the foregoing descriptions and the associated drawings. Therefore, it is to be understood that this disclosure is not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A capacitive liquid crystal (LC) biosensor for sensing a target biological agent, the capacitive LC biosensor comprising:
   a support board;
   a flow channel positioned on the support board, the flow channel having an inlet port positioned at a first end and an exit port positioned at a second end;
   at least two electrode pads disposed in the flow channel, each of the electrode pads including respective pairs of electrodes;
   an electricity source connected to the at least two electrode pads; and
   an LC sensor array positioned within the flow channel, wherein the LC sensor array comprises:
      a plurality of wells positioned on the at least two electrode pads such that multiple ones of the plurality of wells are associated with each of the electrode pads;
      an organic LC phase positioned within each of the plurality of wells; and
      an aqueous phase comprising an analyte positioned above the organic LC phase within the plurality of wells.

2. The capacitive LC biosensor of claim 1, wherein each of the pairs of electrodes comprise gold electrodes.

3. The capacitive LC biosensor of claim 2, wherein at least one of the pairs of electrodes comprises a gold interdigitated electrode.

4. The capacitive LC biosensor of claim 1, wherein the target biological agent comprises at least one of a nucleic acid, a protein, a small molecule, or any combination thereof.

5. The capacitive LC biosensor of claim 4, wherein the target biological agent comprises a nucleic acid or a protein, and wherein the LC biosensor further comprises:
   a nucleic acid extraction portion, the nucleic acid extraction portion being configured to extract nucleic acid from a sample to form an extracted nucleic acid; and a nucleic acid amplification portion, the nucleic acid amplification portion being configured to amplify the extracted nucleic acid for sensing via the LC biosensor.

6. The capacitive LC biosensor of claim 4, wherein the target biological agent comprises a nucleic acid or a protein, and wherein the analyte comprises a single-stranded DNA molecule anchored to a cholesterol molecule.

7. The capacitive LC biosensor of claim 4, wherein the target biological agent comprises a small molecule, and wherein the analyte comprises a small molecule receptor anchored to a cholesterol molecule.

8. A capacitive liquid crystal (LC) biosensor device, comprising:
an exterior portion comprising a display; and
an interior portion comprising:
a capacitive LC biosensor,
a sample input portion upstream of the capacitive LC biosensor, and
a wicking cap downstream of both the sample input portion and the capacitive LC biosensor,
wherein the capacitive LC biosensor comprises:
a support board;
a flow channel positioned on the support board, the flow channel having an inlet port positioned at a first end and an exit port positioned at a second end;
at least two electrode pads disposed in the flow channel, each of the electrode pads including respective pairs of electrodes;
an electricity source connected to the at least two electrode pads; and
an LC sensor array positioned within the flow channel,
wherein the LC sensor array comprises:
a plurality of wells positioned on the at least two electrode pads such that multiple ones of the plurality of wells are associated with each of the electrode pads;
an organic LC phase positioned within each of the plurality of wells; and
an aqueous phase comprising an analyte positioned above the organic LC phase within the plurality of wells.

9. The device of claim 8, wherein the device is paper-based and operates via passive lateral flow.

10. The device of claim 8, wherein the capacitive LC biosensor further comprises at least two instrumentation connectors for connecting to the exterior portion of the device.

11. A method for sensing a target biological agent, the method comprising:
providing a capacitive liquid crystal (LC) biosensor;
adding a sample to the capacitive LC biosensor; and
identifying whether a state change occurred in association with adding the sample to the capacitive LC biosensor in order to determine whether the target biological agent is present in the sample,
wherein providing the LC biosensor comprises providing the capacitive LC biosensor to include:
a support board;
a flow channel positioned on the support board, the flow channel having an inlet port positioned at a first end and an exit port positioned at a second end;
at least two electrode pads disposed in the flow channel, each of the electrode pads including respective pairs of electrodes;
an electricity source connected to the at least two electrode pads; and
an LC sensor array positioned within the flow channel,
wherein the LC sensor array comprises:
a plurality of wells positioned on the at least two electrode pads such that multiple ones of the plurality of wells are associated with each of the electrode pads;
an organic LC phase positioned within each of the plurality of wells; and
an analyte-containing aqueous phase positioned above the organic LC phase within the plurality of wells.

12. The method of claim 11, further comprising multiplexing the method in order to generate readable barcodes.

13. The method of claim 11, wherein each of the pairs of electrodes comprise gold electrodes.

14. The method of claim 13, wherein at least one of the pairs of electrodes comprises a gold interdigitated electrode.

15. The method of claim 11, wherein the target biological agent comprises at least one of a nucleic acid, a protein, a small molecule, or any combination thereof.

16. The method of claim 15, wherein the target biological agent comprises a nucleic acid or a protein, and wherein, prior to identifying whether a state change occurred in association with adding the sample to the capacitive LC biosensor in order to determine whether the target biological agent is present in the sample, the method further comprises:
extracting a sample nucleic acid from the sample to form an extracted nucleic acid; and
amplifying the extracted nucleic acid for sensing via the capacitive LC biosensor.

17. The method of claim 15, wherein the target biological agent comprises a nucleic acid or a protein, and wherein the analyte comprises single-stranded DNA anchored to a cholesterol molecule.

18. The method of claim 17, wherein the target biological agent comprises a nucleic acid or a protein, and wherein identifying whether a state change occurred in association with adding the sample to the capacitive LC biosensor comprises capacitively sensing DNA hybridization.

19. The method of claim 15, wherein the target biological agent comprises a small molecule, and wherein the analyte comprises a small molecule receptor anchored to a cholesterol molecule.

* * * * *